(12) United States Patent
Sessa et al.

(10) Patent No.: US 7,767,641 B2
(45) Date of Patent: Aug. 3, 2010

(54) REGULATOR OF ENDOTHELIAL CELL FUNCTION AND VESSEL REMODELING

(75) Inventors: William C. Sessa, Madison, CT (US); Lisette Acevedo, San Diego, CA (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/554,252

(22) PCT Filed: Apr. 23, 2004

(86) PCT No.: PCT/US2004/012354

§ 371 (c)(1),
(2), (4) Date: Jan. 18, 2007

(87) PCT Pub. No.: WO2004/096846

PCT Pub. Date: Nov. 11, 2004

(65) Prior Publication Data

US 2007/0123456 A1    May 31, 2007

Related U.S. Application Data

(60) Provisional application No. 60/465,149, filed on Apr. 24, 2003.

(51) Int. Cl.
*A61K 38/17* (2006.01)
(52) U.S. Cl. .................. 514/2; 514/8; 514/12
(58) Field of Classification Search ........................ None
See application file for complete search history.

(56) References Cited

U.S. PATENT DOCUMENTS

| | | | |
|---|---|---|---|
| 5,877,293 A | 3/1999 | Adair et al. | |
| 5,886,152 A | 3/1999 | Nakatani et al. | |
| 6,054,297 A | 4/2000 | Carter et al. | |

FOREIGN PATENT DOCUMENTS

WO    WO 00/60083    10/2000

OTHER PUBLICATIONS

Acevedo et al., "A New Role For Nogo As A Regulator Of Vascular Remodeling" Nature Medicine, 10(4):382-388 (2004).
Anderson, "The Caveolae Membrane System" Annu. Rev. Biochem., 67:199-225 (1998).
Goldberg et al., "Nogo In Nerve Regeneration" Nature, 403(6768):369-370 (2000).
Li Qin et al., "Link Of A New Type of Apoptosis-Inducing Gene ASY/NOG-B To Human" Oncogene, 20(30):3929-3936 (2001).
Oertle et al., "Do Cancer Cells Die Because Of Nogo-B?" Oncogene, 22(9):1390-1399 (2003).
Oertle et al., "Genomic Structure And Functional Characterisation Of The Promoters Of Human And Mouse Nogo/rtn4" J. Mol. Biol., 325 (2):299-323 (2003).
Prinjha et al., "Inhibitor Of Neurite Outgrowth In Humans" Nature, 403(6768):383-384 (2000).
Ross, "The Pathogenesis of Atherosclerosis: A Perspective For The 1990s" Nature, 362:801-809 (1993).
Shaul and Anderson, "Role of Plasmalemmal Caveolae In Signal Transduction" Am. J. Physiol., 275(5):L843-851 (1998).
Ward et al., "Arterial Remodeling Mechanisms And Clinical Implications" Circulation, 102:1186-1191(2000).
Watari and Yutsudo, "Multi-Functional Gene ASY/Nogo/RTN-X/RTN4: Apoptosis, Tumor Suppression, And Inhibition Of Neuronal Regeneration" Apoptosis, 8:5-9 (2003).

*Primary Examiner*—Prema Mertz
(74) *Attorney, Agent, or Firm*—Drinker Biddle & Reath LLP

(57) ABSTRACT

The present invention relates to previously unknown biological roles of Nogo-B. We have discovered that Nogo-B is a component of endothelial cells. We have also discovered that Nogo-B is highly expressed in intact blood vessels. The amino terminus of Nogo-B promotes the adhesion, spreading and migration of endothelial cells and plays a role in vascular remodeling. Thus, Nogo-B is a novel regulator of vascular homeostasis and remodeling. The present invention provides compositions comprising Nogo-B and fragments and fusion proteins thereof. The present invention also relates to nucleic acids encoding Nogo-B and fragments and fusion proteins thereof, as well as vectors and cells comprising such nucleic acids. The present invention also relates to antibodies specific for Nogo-B and fragments and fusion proteins thereof. The present invention also provides methods for preventing, detecting and treating Nogo-B-related diseases, disorders and conditions.

3 Claims, 16 Drawing Sheets

Expression of Nogo isoforms in vascular cells

Expression of Nogo isoforms in blood vessels

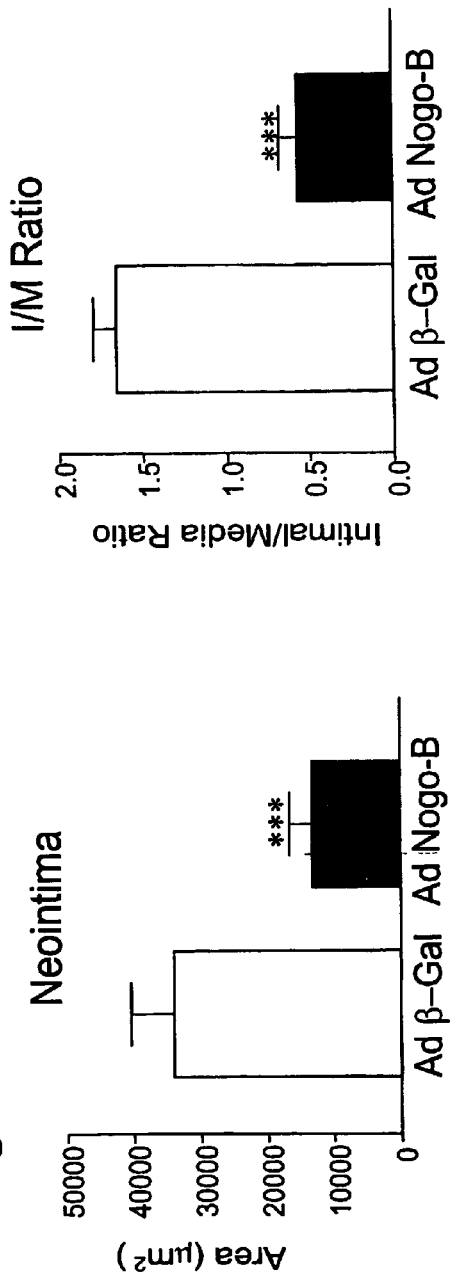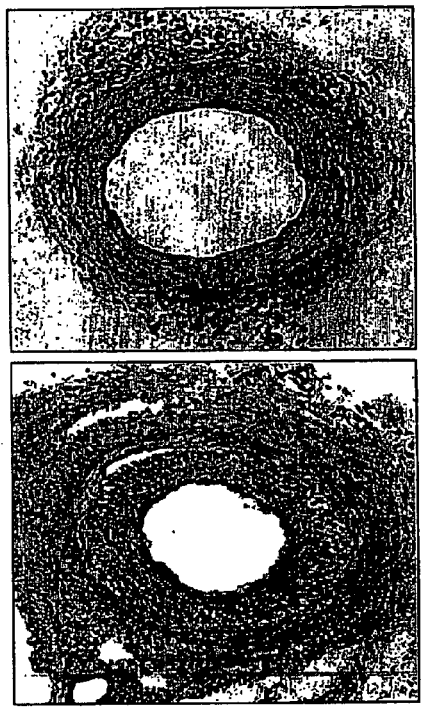
Figure 15

REGULATOR OF ENDOTHELIAL CELL FUNCTION AND VESSEL REMODELING

This application is a National Phase filing under 35 U.S.C. §371 of International Application PCT/US2004/012354, filed Apr. 23, 2004, which designates the United States, is published in English and claims priority under 35 U.S.C. § 119(e) from United States Provisional Application 60/465, 149, filed Apr. 24, 2003. The entire disclosure of the applications are incorporated herein by reference.

FIELD OF THE INVENTION

This invention relates to compositions and methods useful for the diagnosis, prevention and treatment of Nogo-B-related diseases and conditions.

More particularly, this invention relates to the Nogo-B protein and fragments thereof and methods of using them.

BACKGROUND

Nogo Proteins

Nogo is the fourth member of the Reticulon family of proteins to be identified, and therefore is sometimes referred to as Reticulon 4 (RTN4). Nogo has three known expressed isoforms called Nogo-A, Nogo-B, and Nogo-C, which all arise from a common nogo gene either through alternative splicing (Nogo-A and Nogo-B) or alternative promoter usage (Nogo-C). See Oertle et al., J. Mol. Biol. 325:299-323 (2003) ("Oertle"). Nogo-A is the full length isoform, which contains 1192 amino acids. Nogo-B is a shorter splice variant. There are two forms of Nogo-B. Nogo-B1 is 373 amino acids in length, and is missing residues 186-1004 of Nogo-A. Nogo-B2 is a minor splice variant that contains an extra 19 amino acids within the amino terminus; however, its protein expression remains undetected (see Oertle). Nogo-C is the shortest isoform, 199 amino acids long, with the first 11 residues being specific to this isoform.

Nogo-A and Nogo-C are highly expressed in the central nervous system (CNS), with Nogo-C additionally found in skeletal muscle, while Nogo-B is found in most tissues. See GrandPre 2000; see also Chen.

Nogo-B

The peripheral roles of Nogo are virtually unknown. Here, we identify Nogo-B as a component of CEM/LR domains in cultured endothelial cells.

Caveolae (or little caves), caveolin-1 enriched membranes (CEM) and "lipid rafts" (LR) represent membrane subcompartments within endothelial cells. They have been implicated in a variety of biological functions including signal transduction. See Anderson, Annu. Rev. Biochem. 67:199-225 (1998) ("Anderson"); see also Shaul and Anderson, Am. J. Physiol. 275:L843-851 (1998) ("Shaul").

The best defined of these subcompartments are caveolae, flask-like invaginations 50-100 nm in diameter within the plasma membrane. Caveolae contain the coat protein caveolin-1.

While caveolae can be defined morphologically, CEM are defined by their biochemical properties. CEM are similar to "lipid rafts", flat lateral assemblies within membranes, except that "lipid rafts" do not contain the coat protein caveolin-1.

For clarity, caveolae, CEM and lipid rafts have been combined herein combine into a biochemically defined subcellular group known as CEM/LR.

CEM/LR are found mostly on the plasma membrane, though they have also been found in the biosynthetic and endocytic pathways. CEM/LR have been implicated in many different cellular processes including signal transduction.

A number of proteins have been identified as components of CEM/LR. As disclosed herein, one of the proteins identified as a component of CEM/LR was Nogo-B, one of three known isoforms of the neuronal outgrowth inhibitor Nogo.

In contrast to the inhibitory action of Nogo-A on cell adhesion and axonal sprouting, as shown herein the amino terminus of Nogo-B promotes the adhesion, spreading and migration of endothelial cells. We also show that Nogo-B is highly expressed in intact blood vessels and plays a role in vascular homeostasis and vascular remodeling. We also show that vascular injury in Nogo-A/B-deficient (knockout) mice promotes exaggerated neointimal proliferation, and that adenoviral-mediated gene transfer of Nogo-B rescues the abnormal vascular expansion in those knockout mice. Thus, Nogo-B is a novel regulator of vascular homeostasis and remodeling, broadening the functional scope of this family of proteins.

SUMMARY OF THE INVENTION

The present invention addresses the above-mentioned newly discovered roles of Nogo-B in vascular homeostasis (or quiescence) and blood vessel remodeling.

In one embodiment, the invention comprises a composition comprising Nogo-B or a fragment of Nogo-B that retains a biological activity of Nogo-B. The composition may comprise full-length Nogo-B.

The composition may comprise Nogo-B from any animal. In a preferred embodiment, the composition comprises human Nogo-B.

In another embodiment, the composition comprises a fragment comprising amino acids 1-200 of Nogo-B. Herein, this fragment is alternatively referred to as "Am-Nogo-B".

In another embodiment, the invention comprises a composition comprising Nogo-B or a Nogo-B fragment that retains Nogo-B biological activity.

In another embodiment, the composition comprises Nogo-B or a fragment thereof and at least one pharmaceutically acceptable carrier.

In another embodiment, the composition comprises Nogo-B or a fragment thereof and at least one other component, including, but not limited too: an excipient, a therapeutic agent, a diagnostic agent and a Nogo-B agonist.

In another embodiment, the Nogo-B or fragment of Nogo-B according to this invention is detectably labelled.

In yet another embodiment, a composition according to this invention may comprise a Nogo-B agonist or antagonist.

In another embodiment, a composition according to this invention may comprise a Nogo-B agonist or antagonist and at least one pharmaceutically acceptable carrier.

In yet another embodiment, a composition according to this invention may comprise a Nogo-B agonist or antagonist that is detectably labelled.

In yet another embodiment, the invention provides fusion proteins comprising Nogo-B or a fragment thereof and an additional component.

In another embodiment, this invention provides nucleic acid molecules that encode Nogo-B, fragments of Nogo-B or Nogo-B fusion proteins. In one embodiment, the nucleic acid molecules according to this invention may be operably linked to an expression control sequence that facilitates expression of the Nogo-B fragment or fusion protein.

In another embodiment, the nucleic acid molecule encoding fragments of Nogo-B or Nogo-B fusion proteins, may be linked to an expression vector.

In an alternative embodiment, the expression vector may be a viral expression vector.

In another embodiment, this invention provides host cells comprising nucleic acids encoding Nogo-B or a fragment or fusion protein thereof. An alternative embodiment of this invention provides host cells comprising a vector according to this invention.

The present invention also provides antibodies or antigen binding antibody fragments specific for Nogo-B. The antibodies may be polyclonal or monoclonal. The antibodies may be human, humanized or chimeric. In addition, the antibodies may act as agonists or antagonists of Nogo-B activity.

The present invention also provides methods for producing Nogo-B or fragments or fusion proteins thereof, compositions comprising Nogo-B or fragments or fusion proteins thereof, and antibodies specific for Nogo-B or fragments or fusion proteins thereof.

The present invention also provides nucleic acid molecules encoding Nogo-B or fragments or fusion proteins thereof. The present invention also provides vectors comprising nucleic acid molecules encoding Nogo-B or fragments or fusion proteins thereof.

The present invention also provides methods for the detection of subjects in need of Nogo-B-related treatment.

The present invention also provides methods for promoting or inhibiting angiogenesis in subjects in need thereof.

The present invention also provides methods of diagnosing, preventing or treating Nogo-B-related diseases, conditions or disorders.

The present invention also provides methods of promoting Nogo-B-facilitated quiescence or homeostasis.

The present invention also provides methods of reducing, preventing, inhibiting or treating neointima formation in subjects in need thereof.

The present invention also provides methods of reducing, preventing, inhibiting or treating vascular injury in subjects in need thereof.

The present invention also provides methods of reducing, preventing, inhibiting or treating vascular injury-induced ischemia in subjects in need thereof.

The present invention also provides methods of reducing, preventing, inhibiting or treating vascular injury-induced vascular narrowing or occlusion in subjects in need thereof.

The present invention also provides methods for promoting endothelial cell spreading, adhesion or migration in subjects in need thereof.

The present invention also provides methods for inhibiting vascular smooth muscle cell migration in subjects in need thereof.

BRIEF DESCRIPTION OF THE DRAWINGS

FIG. 1 shows an agarose gel slab in which RT-PCR products (from RT-PCR of total RNA isolated from EA.hy.926 and HUVEC cells (two kinds of human endothelial cells)) were electrophoresed alongside Nogo-A and Nogo-B plasmids. Lane 1: Plasmids. Lane 2: RT-PCR products from EA.hy.926 cells. Lane 3: RT-PCR products from HUVEC cells. Top to Bottom: Nogo-A, Nogo-B, Nogo-B2 and β-Actin (used as a control), respectively.

FIG. 2 shows the results of a Western blot using an antibody that detects amino acids 1-18 of both Nogo-A and Nogo-B. FIG. 2 shows that Nogo-B, and not Nogo-A, is expressed in EA.hy.926, HUVEC and HAVSMC (primary vascular smooth muscle cells). Lane 1: COS-7 cells transfected with either Nogo-A or Nogo-B cDNA as antibody controls. Lane 2: protein from EA.hy.926 cells. Lane 3: protein from HUVEC cells. Lane 4: protein from HAVSMC. Top to Bottom: Nogo-A, Nogo-B, Hsp90 (used as a loading control), respectively.

FIG. 3 is a bar graph showing the percentage of cell spreading promoted by PBS (bar 1), GST (bar 2), GST-Am-Nogo-B (bar 3) and GST-Nogo-66 (bar 4) in EA.hy.926 endothelial cells or COS-7 cells. FIG. 3 shows that GST-Am-Nogo-B promotes endothelial cell (EA.hy.926 cells) spreading but not COS cell spreading, while GST-Nogo-66 has no significant effect on the spreading of either cell type. Neither PBS or GST alone has any effect on cell spreading. Black bars represent EA.hy.926 cells and gray bars represent COS cells.

FIG. 4 is a bar graph showing that GST-Am-Nogo-B promotes adhesion in EA.hy.926 and HUVEC endothelial cells. Neither PBS or GST alone has any effect on cell adhesion. Bar 1: PBS. Bar 2: GST. Bar 3: GST-Am-Nogo-B. Black bars represent EA.hy.926 cells and gray bars represent HUVEC cells.

FIG. 5 is a bar graph showing that GST-Am-Nogo-B promotes adhesion in EA.hy.926 cells in a dose-dependent manner. Bars 1-5: 2.5 pmol, 12.5 pmol, 25 pmol, 125 pmol and 250 pmol GST-Am-Nogo-B, respectively. Black bars represent GST-Am-Nogo-B and white bars represent GST alone.

FIG. 6 is a bar graph showing the number of cells that have migrated across membranes in Boyden chambers in response to PBS (control, bar 1), GST (bar 2), 1 nanomolar (nM), 10 nM or 100 nM GST-Am-Nogo-B (bars, 3, 4 and 5, respectively), and 1.1 nM VEGF (positive control, bar 6). FIG. 6 shows that GST-Am-Nogo-B, but not GST alone, increased endothelial cell (HUVEC) migration in a dose-dependant manner. Each value represents mean of SEM (n=3), p<0.05.

FIG. 7 shows an agarose gel slab in which RT-PCR products (from RT-PCR of total RNA isolated from murine brain and in various murine blood vessels: femoral artery, carotid artery, thoracic aorta and abdominal aorta) were electrophoresed to visualize the presence of Nogo mRNA. Lane 1: Brain. Lane 2: femoral artery. Lane 3: carotid artery. Lane 4: thoracic aorta. Lane 5: abdominal aorta. Top to Bottom: Nogo-B, Nogo-B2, Nogo-A, Nogo-C and β-Actin (used as a control), respectively. FIG. 7 shows that Nogo-A, -B, -B2 and -C mRNA were present in all murine tissues tested.

FIG. 8 shows the results of a Western blot using an antibody that detects amino acids 1-18 of both Nogo-A and Nogo-B, and another antibody that detects the Nogo-A protein only. Lane 1-2: COS-7 cells transfected with Nogo-A and Nogo-B cDNA (as antibody controls), respectively. Lane 3: Brain. Lane 4: femoral artery. Lane 5: carotid artery. Lane 6: aorta. Top to Bottom: Nogo-A, Nogo-B, β-Actin (used as a control), respectively. FIG. 8 shows that Nogo-B, and not Nogo-A, is expressed in murine femoral arteries, carotid arteries and aortas. Conversely, Nogo-A, and not Nogo-B, is found in murine brains.

FIG. 9 shows the results of a Western blot using an antibody that detects Nogo-A, and another antibody that detects the Nogo-B. Lane 1: Brain. Lane 2: wild-type (see below) aorta. Lane 3: Nogo-A/Nogo-B-deficient aorta. Top to Bottom: Nogo-B, Nogo-A and β-Actin (used as a control), respectively. FIG. 9 shows that Nogo-B, but not Nogo-A, is endogenously expressed in murine wild-type aortas. Conversely, Nogo-A, but not Nogo-B, is endogenously expressed in murine brains. Neither Nogo-A nor Nogo-B is expressed in the aortas of Nogo-A/Nogo-B-deficient mice (i.e. from mice "trapped" with β-galactosidase).

FIG. 11C shows representative hematoxylin and eosin (H & E) stained femoral arteries of Nogo-A/B(+/+) and (−/−) mice three weeks after injury. Three weeks after injury, Nogo A/B (−/−) mice exhibited strikingly enhanced neointima formation compared to control mice, and in some cases, complete occlusion of the femoral artery was seen.

FIG. 12A: Representative BrdU immunostaining in vessels from control (C57BL/6J; Nogo-B (+)) mice and Nogo-A/Nogo-B (−/−) mice, two weeks after injury. Vessels from Nogo-A/Nogo-B (−/−) mice show enhanced cellular proliferation (bottom panel), while vessels from control mice show reduced cellular proliferation (top panel). FIG. 12B: Quantitation of BrdU labeling in different layers (intima, media, adventitia) or whole femoral arteries at 2 weeks after injury. Data are expressed as mean±SEM with 10 sections of 5 arteries analyzed, p<0.05.

FIG. 13 shows representative hematoxylin and eosin (H & E; top) and elastic Van Geisson (EVG, for elastic lamina, bottom) stained femoral arteries of wild-type mice transduced with Ad-β-gal or Ad-Nogo-B. Transduction of wild-type vessels with Ad Nogo-B decreases neointimal proliferation after injury.

FIG. 14 shows that transduction of wild-type vessels with Ad Nogo-B decreases neointimal proliferation after injury.

FIG. 15. Ad-Nogo-B-HA rescues abnormal neointima formation in Nogo-A/B (−/−) mice. FIG. 15A & B: Intimal area (FIG. 15A) and intima/media (I/M) ratio (FIG. 15B) were quantified morphometrically three weeks after injury. Vessels transduced with Ad-β-gal showed an increase in intimal expansion (intimal area (FIG. 15A) and I/M ratio (FIG. 15B). Conversely, vessels transduced with Ad-Nogo-B showed a decrease in intimal expansion (intimal area (FIG. 3A) and I/M ratio (FIG. 15B). FIG. 15C: Murine blood vessels were injured and immediately thereafter transduced with either Ad-β-gal (which does not rescue Nogo-B deficiency) or Ad-Nogo-B (which does rescue Nogo-B deficiency. Three weeks after injury, neointima is thickened (greater neointima proliferation) in vessels transduced with Ad-β-gal, compared with vessels transduced with Ad-Nogo-B.

FIG. 16 is a graphic display that shows that the loss of Nogo-B impairs blood flow recovery after surgery. FIG. 16A: gross examination of the limbs using the YCS clinical score for spontaneous mobility at 3, 14 and 28 days further demonstrated impaired recovery of blood flow to the lower limb of Nogo-A/B (−/−) mice. FIG. 16B: the measurement of lower limb blood flow was performed using a Deep Laser Doppler prior to surgery as well as 30 minutes, 14 and 28 days after surgery to induce ischemia.

DETAILED DESCRIPTION OF THE INVENTION

Figure 1:
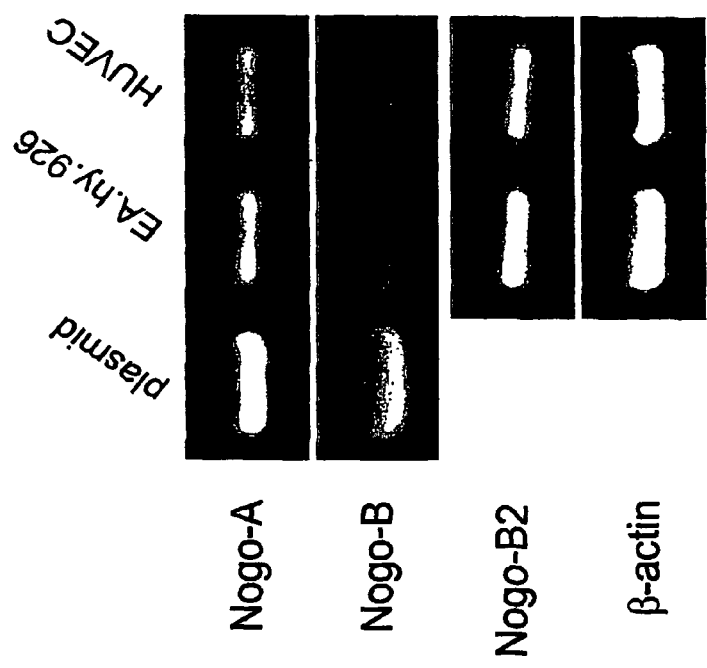
FIG. 1. Identification of Nogo mRNA in endothelial cells.

The peripheral roles of Nogo were, up to now, virtually unknown. Here, we have identified Nogo-B as a component of CEM/LR domains in cultured endothelial cells. In contrast to the inhibitory action of Nogo-A on cell adhesion and axonal sprouting, the amino terminus of Nogo-B promotes the adhesion, spreading and migration of endothelial cells. We also show that Nogo-B is highly expressed in intact blood vessels and plays a role in vascular homeostasis and vascular remodeling. We also show that vascular injury in Nogo-A/B-deficient (knockout) mice promotes exaggerated neointimal proliferation, and that adenoviral-mediated gene transfer of Nogo-B rescues the abnormal vascular expansion in those knockout mice. Thus, Nogo-B is a novel regulator of vascular homeostasis and remodeling, broadening the functional scope of this family of proteins.

The term Nogo-B refers to a 373 amino acid isoform of Nogo. The invention contemplates compositions and methods comprising the Nogo-B polypeptides encoded by nucleic acids having GenBank accession numbers: (1) human Nogo-B: GenBank accession number AY102277 (Oertle et al., J. Mol. Biol. 325(2):299-323 (2003); mouse Nogo-B: AY102281 (Oertle et al., J. Mol. Biol. 325(2):299-323 (2003); Human Nogo-B2 AY102278 (Oertle et al., J. Mol. Biol. 325(2):299-323 (2003); and Mouse Nogo-B2: AY102284 (Oertle et al., J. Mol. Biol. 325(2):299-323 (2003) as well as species homologs of these polypeptides. Likewise, compositions and methods of the invention contemplate Nogo-B polypeptides having the amino acid sequence set forth in GenBank accession numbers: (1) human Nogo-B: AAM64246 (Oertle et al., J. Mol. Biol. 325(2):299-323 (2003); and mouse Nogo-B: AAM77069 (Jin, et al., Unpublished (2002) and species homologs of said polypeptides. The above-mentioned GenBank sequence submissions and the Oertle et al. reference are hereby incorporated by reference in their entirety.

All blood vessels contain a similar organization consisting of three layers: the tunica intima, media, and adventitia.

The tunica intima ("intima") is the innermost layer of the vessel. The intima contains primarily endothelial cells. Endothelial cells are the main regulators of vascular homeostasis because they form an interface between blood and tissue, interacting with both circulating cells and cells of the vascular wall. As an interface, they are susceptible to changes in blood composition and blood flow; therefore, endothelial cells are the main responders to these changes and play a critical role in the mechanisms underlying the development of vascular disorders.

The medial layer is called the tunica media ("media"). The media contains primarily vascular smooth muscle cells. Vascular smooth muscle cells are the effector cells of the vessel, contracting or relaxing to alter the diameter of a blood vessel in response to various agents.

The outermost layer of a blood vessel is the tunica adventitia ("adventitia").

These three layers are continuously working together to respond acutely to any changes in blood flow as well as adaptive responses to sustained alterations in flow through vessel remodeling.

Blood vessels undergo alterations to various phenomenon, e.g., injury or disease. These alterations are accomplished by either outward or inward remodeling of the vessel. Outward remodeling increases the vessel diameter, while inward remodeling decreases lumen diameter. Remodeling also occurs under pathological conditions such as hypertension and in response to injury as in atherosclerosis (an inflammatory process by which the intima becomes thickened with lipid rich gruel and connective tissue), restenosis (a re-narrowing of the vessel lumen), and luminal stenosis after transplant vasculopathy.

We have discovered that Nogo-B is an important regulator of inward remodeling of blood vessels, In one embodiment, the invention comprises a composition comprising Nogo-B or a fragment of Nogo-B that retains a biological activity of Nogo-B. The composition may comprise full-length Nogo-B.

The composition may comprise Nogo-B from any animal. In a preferred embodiment, the composition comprises human Nogo-B.

In a preferred embodiment, the composition comprises a fragment comprising amino acids 1-200 of Nogo-B. Herein, this fragment is alternatively referred to as "Am-Nogo-B".

In a preferred embodiment, the invention comprises a composition comprising Nogo-B or a Nogo-B fragment that retains Nogo-B biological activity that includes, but is not limited to: (1) promoting in a vascular endothelial cell cellular adhesion, cellular spreading, cellular migration and/or proliferation; (2) inhibiting in a vascular smooth muscle cell migration; (3) reducing pathological vascular remodeling; (4) reducing neointima formation in a blood vessel; (5) promoting angiogenesis; (6) maintaining vascular homeostasis; and (7) promoting wound healing.

In another embodiment, the composition comprises Nogo-B or a fragment thereof and at least one pharmaceutically acceptable carrier.

In another embodiment, the composition comprises Nogo-B or a fragment thereof and at least one other component, including, but not limited too: an excipient, a therapeutic agent, a diagnostic agent and a Nogo-B agonist.

Excipients according to this invention include, but are not limited to those excipients that are described in the *Handbook of Pharmaceutical Excipients*, published jointly by the American Pharmaceutical Association and the Pharmaceutical Society of Great Britain.

Therapeutic agents according to this invention include, but are not limited too: anti-inflammatory agents, anti-coagulant agents, anti-fibrotic agents, anti-hypertensives, lipid-lowering agents and immunosuppressive agents.

In another preferred embodiment, the Nogo-B or fragment of Nogo-B according to this invention is detectably labelled. Detectable labels according to this invention include, but are not limited to: radiolabels, enzyme labels, toxins, magnetic agents or drug conjugates. Detectable labels according to this invention include, but are not limited to, the following substances: enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^3$H, $^{14}$C, $^{15}$N, $^{35}$S, $^{90}$Y, $^{99}$Tc, $^{111}$In, $^{125}$I, and $^{131}$I.

In yet another embodiment, a composition according to this invention may comprise a Nogo-B agonist or antagonist. Examples of antagonists according to this invention include, but are not limited to: antibodies, including monoclonal antibodies, siRNA, antisense nucleic acids, ribozymes, small molecule antagonists, including soluble peptides, and peptide mimetics. In another embodiment, a composition according to this invention may comprise a Nogo-B agonist or antagonist and at least one pharmaceutically acceptable carrier. In yet another embodiment, the Nogo-B agonist or antagonist is detectably labelled.

In yet another embodiment, the invention provides fusion proteins comprising Nogo-B or a fragment thereof and an additional component. The additional component may be a heterologous protein or fragment thereof. Examples of additional components of a fusion protein according to this invention include, but are not limited to: targeting agents (e.g., agents that target the fusion protein to vasculature, endothelial cells, or vascular smooth muscle cells), imaging agents; glutathione-S-transferase (GST), alkaline phosphatase (AP), immunoglobulin Fc portions and cell permeable peptides.

In another embodiment, this invention provides nucleic acid molecules that encode fragments of Nogo-B or Nogo-B fusion proteins. In some embodiments, the fragment may be used as a probe to identify and/or isolate a nucleic acid encoding Nogo-B. In some embodiments, the fragment that retains a biological activity of Nogo-B. The nucleic acid molecule can be RNA or DNA. If DNA, the nucleic acid can be cDNA or genomic DNA.

The nucleic acid probes may comprise a label group attached thereto, e.g., a radioisotope, a fluorescent compound, an enzyme, or an enzyme co-factor. Such probes can be used as a part of a diagnostic kit for identifying cells or tissues expressing Nogo-B.

Nucleic acid fragments of at least 6 nucleotides (e.g., at least 7, 8 9 or 10) in length can be used as primers in PCR, primer extension and the like. Of course, larger fragments having at least 25, 30, 35, 40, 45, 50, 100, 150, 200, 250, 300, 350, 400, 450, 500 or more nucleotides are also useful, and at times preferred, as will be appreciated by the skilled worker.

The nucleic acid molecules according to this invention may be operably linked to an expression control sequence that facilitates expression of the Nogo-B fragment or fusion protein.

In yet another embodiment, the present invention provides vectors that comprise nucleic acid molecules of the invention. The recombinant nucleic acid molecules and more particularly, the expression vectors of this invention may be used to express Nogo-B protein or fragments or fusion proteins thereof.

Nucleic acid sequences may be expressed by operatively linking them to an expression control sequence in an appropriate expression vector and employing that expression vector to transform an appropriate unicellular host. Expression control sequences are sequences which control the transcription, post-transcriptional events and translation of nucleic acid sequences. Such operative linking of a nucleic sequence of this invention to an expression control sequence, of course, includes, if not already part of the nucleic acid sequence, the provision of a translation initiation codon, ATG or GTG, in the correct reading frame upstream of the nucleic acid sequence.

A wide variety of host/expression vector combinations may be employed in expressing the nucleic acid sequences of this invention. Useful expression vectors, for example, may consist of segments of chromosomal, non-chromosomal and synthetic nucleic acid sequences. Useful expression vectors for bacterial and eukaryotic host cells, such as yeast or mammalian cells, may be used and are well known in the art. Expression in mammalian cells, for example, can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL941.

In addition, any of a wide variety of expression control sequences may be used in these vectors to express the DNA sequences of this invention. A multitude of expression control sequences are available in the art and may be selected to direct appropriate expression of the nucleic acids and/or polypeptides of the invention. For instance, any of a wide variety of expression control sequences-sequences that control the expression of a DNA sequence when operatively linked to it may be used in vectors to express sequences encoding the polypeptides of this invention. Expression control sequences that control transcription include, e.g., promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation and/or mRNA degradation.

Many examples of useful expression control sequences—including constitutive, inducible and tissue-specific promoter and/or enhancer sequences—are known to control the expression of genes of prokaryotic or eukaryotic cells and their viruses. Promoters suitable for use with prokaryotic hosts include the regulated beta-lactamase, lactose, tryptophan (trp) and lambda phage promoter systems, alkaline phosphatase, and hybrid promoters such as the tac promoter. Promoters for use in bacterial systems will preferably contain a Shine-Dalgarno (S.D.) sequence operably linked to the DNA encoding the polypeptide of interest. Examples of suitable promoters for use in yeast hosts include the promoters for 3-phosphoglycerate kinase or other glycolytic enzymes. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Transcription from vectors in mammalian host cells may be controlled, for example, by promoters obtained from the genomes of viruses such as polyoma virus, fowlpox virus, adenovirus (such as Adenovirus 2 or 5), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems. Other useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage 1, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. the nucleic acid molecule encoding fragments of Nogo-B or Nogo-B fusion proteins, may be linked to an expression vector. Such vectors are useful, e.g., for amplifying the polynucleotides in host cells to create useful quantities thereof. In other embodiments, the vector is an expression vector wherein the polynucleotide of the invention is operatively linked to a polynucleotide comprising an expression control sequence. Such vectors are useful for recombinant production of polypeptides of the invention. In an alternative embodiment, the expression vector may be a viral expression vector. Examples of viral expression vectors according to this invention include, but are not limited to: AAV (adeno-associated virus), lentivirus, adenovirus, retrovirus, and Herpes virus vectors.

In another embodiment, this invention provides host cells comprising nucleic acids encoding Nogo-B or a fragment or fusion protein thereof. An alternative embodiment of this invention provides host cells comprising a vector according to this invention. Such host cells are useful for amplifying the nucleic acids and also for expressing Nogo-B or a fragment thereof encoded by the nucleic acids.

The invention provides antibodies that bind specifically to Nogo-B. The antibodies can be specific for linear epitopes, discontinuous epitopes, or conformational epitopes of Nogo-B, either as present on the polypeptide in its native conformation or, in some cases, as present on the polypeptides as denatured, as, e.g., by solubilization in SDS.

An antibody of this invention refers to a full antibody, e.g., an antibody comprising two heavy chains and two light chains, or to an antigen-binding fragment of a full antibody. Such fragments include, but are not limited to, those produced by digestion with various proteases, those produced by chemical cleavage and/or chemical dissociation, and those produced recombinantly, so long as the fragment remains capable of specific binding to an antigen. Among these fragments are Fab, Fab', F(ab')$_2$ Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide.

An antibody of this invention can be a murine or hamster antibody or a homolog thereof, or a fully human antibody. An antibody of this invention can also be a humanized antibody, a chimeric antibody, an antibody fusion, an diabody, an intrabody, or a single-chained antibody. An antibody of this invention can be of any isotype and subtype, for example, IgA (e.g., IgA1 and IgA2), IgG (e.g., IgG1, IgG2, IgG3 and IgG4), IgE, IgD, IgM, wherein the light chains of the immunoglobulin may be of type kappa or lambda. While the useful antibodies are generally monoclonal, polyclonal antibodies from mice, rabbits, turkeys, or sheep may also be used.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as will be appreciated by the skilled worker.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies.

Methods of making antibodies, including monoclonal antibodies, are well-known in the art. The antibodies of the invention may be made by any such methods including but not limited to immunizing a non-human animal with Nogo-B or an immunogenic fragment thereof and recovering the antibody, immortalization technology (including hybridoma technology), phage display and the like. Nucleic acid molecules encoding the heavy and light chains of antibodies of the invention may be isolated according to methods well known in the art and expressed recombinantly in a host cell.

As a response to vascular injury to the luminal surface of a vessel, either through mechanical injury (balloon angioplasty leading to restenosis) or endothelial dysfunction (atherosclerosis), the intima expands and thickens. This neointima becomes a complex milieu containing extracellular matrix, vascular smooth muscle which expand out from the underlying tunica media, inflammatory cells invading from the circulation, and bone marrow-derived progenitor cells recruited to the site of injury.

Neointima formation begins immediately after injury. Neointima formation involves numerous types of cells, including vascular smooth muscle cells and endothelial cells. After injury, vascular smooth muscle cells begin to proliferate and migrate into the lumen of the vessel. Smooth muscle cells are seen in the intima within 8 days of injury. By 4 weeks their migration and proliferation into the intima has peaked.

The endothelium also plays a role in response to vascular injury as neointimal thickness is correlated to the rate of re-endothelialization after injury.

We have discovered that residues 1-200 of Nogo-B, which make up the amino terminus, is a functional domain of Nogo-B. This domain is referred to herein as Am-Nogo-B.

We have also discovered Am-Nogo-B enhances endothelial cell spreading.

We have also discovered that Am-Nogo-B also dose-dependently increases endothelial and vascular smooth muscle cell adhesion.

We have also discovered, moreover, that Am-Nogo-B functions as a chemoattractant for endothelial cells by dose-dependently enhancing their migration.

Conversely, we have discovered that Am-Nogo-B inhibits migration of vascular smooth muscle cells.

Cell spreading and adhesion are critical events in maintaining homeostasis, because they are important for the assembly of cells into three dimensional structures and the maintenance of these structures through either cell-cell or cell-substrate interactions. Specifically within the vasculature, adhesion and spreading are important not only for laying the foundation for new vessels, but also for vessel maturation. Therefore, Nogo-B functions in maintaining vessel structure (homeostasis) by promoting vascular cell adhesion and spreading.

Furthermore, the migration of vascular cells is one of the key mechanisms involved in arterial remodeling. Accordingly, Nogo-B also functions in vascular remodeling. Thus, Nogo-B functions to maintain vessel integrity after injury, since it inhibits smooth muscle cell chemotaxis, while also facilitating repair of the injured vessel, in its role promoting endothelial cell chemotaxis.

Thus, we have discovered that Nogo-B, is a novel regulator of vascular cell spreading, adhesion, and migration, providing the first evidence for function of Nogo outside of the nervous system and showing that Nogo can function as an enhancer as well as inhibitor.

We have also discovered a role for Nogo-B as a mediator of vascular remodeling. A lack of Nogo-B correlates with increased neointimal expansion. After vascular injury in normal mice, there is a dramatic loss of Nogo-B expression in the media at 10 days, which continues up to 21 days where there is little Nogo-B detected in the media as well as neointima. Furthermore, we show that there is a significant increase in neointima formation in injured vessels from Nogo-A/B (−/−) mice. In some vessels the neointima expansion was so severe that the vessel became occluded. The toes of Nogo-A/B (−/−) mice were black, consistent with a decrease of blood flow to the lower limb due to a narrowing of the vessel lumen. The role of Nogo-B in neointimal formation is further established by the correction of the enhanced neointimal phenotype of Nogo-A/B (−/−) mice when injured vessels are adenovirally transduced with Nogo-B.

The increased neointima formation observed in Nogo-A/B (−/−) injured arteries may be due to enhanced vascular smooth muscle cell migration and/or proliferation as well as impaired endothelial cell migration and/or proliferation. Therefore, we have discovered that Nogo-B functions as a negative regulator by placing a brake on the migration of vascular smooth muscle cells that comprise the growing neointima.

Although the mechanisms of Nogo-B function in vessel remodeling remain to be completely elucidated, the identification of a role for Nogo-B in neointima formation provides a new therapeutic target for vascular diseases involving luminal remodeling, such as restenosis after percutaneous transluminal angioplasty.

Because these results were consistent with Nogo-B being a mediator of vessel remodeling, we examined the role of Nogo-B in neointima formation after vascular injury. Nogo-B also plays a role in vessel remodeling, as its expression is regulated during neointima formation, and the loss of Nogo-A/B results in a greatly enhanced intimal expansion; moreover, reconstitution of vessels with Nogo-B abolished the enhanced neointimal phenotype seen in Nogo-A/B (−/−) mice. Therefore, removal of the Nogo-B constraint leads to enhanced neointima and in some cases occlusion of the vessel. Providing further evidence for Nogo-B in this response, adenoviral reconstitution of vessels from Nogo-A/B (−/−) mice with Nogo-B abolished the enhanced neointimal phenotype seen in these knockout mice.

We have discovered adenoviral overexpression of Nogo-B within the vessel wall in wild-type mice reduces intimal expansion after vascular injury.

We have discovered that Nogo-B can also act as a negative regulator by promoting the migration of endothelial cells back into the site of injury since re-endothelialization leads to a cessation of neointimal progression.

Conversely, we have also discovered that Nogo-B can halt intimal expansion by decreasing the migration of vascular smooth muscle into the lumen.

Thus, we have discovered that Nogo-B functions as a chemoattractant for endothelial cells by dose-dependently increasing their migration. But Nogo-B functions in the opposite way with vascular smooth muscle cells because it inhibits the migration of vascular smooth muscle cells.

We have also discovered that Nogo-B inhibits vascular smooth muscle cell migration as it relates to cell proliferation.

Because Am-Nogo-B is a positive regulator of endothelial cell migration, Nogo-B functions in angiogenesis as well. During angiogenesis, vessels endothelial cells need to proliferate and migrate to lay the foundation for neo-vessels. A further embodiment of the invention relates to the role of Nogo-B as therapeutic target for vascular disease. The role of Nogo as a mediator of luminal vessel remodeling makes it a novel therapeutic target for clinically relevant vascular diseases such as restenosis, stenosis after transplant vasculopathy, and atherosclerosis. Since Nogo-B functions as a brake, augmenting the expression of Nogo-B or Am-Nogo-B decelerates the luminal remodeling and neointima formation that occurs in these diseases of vessel injury. Restenosis, or a renarrowing of the lumen, occurs in 30% to 60% of patients where a successful angioplasty has been performed. Luminal stenosis in transplant vasculopathy is the most common cause of graft failure and death after heart transplantation. It is characterized by diffuse angiographic luminal narrowing that is not amenable to revascularization after transplant. See Ward et al., Circulation 102:1186-1191 (2000). Both of these conditions lead to inward or constrictive remodeling within the vessel marked by neointimal thickening. See Van Belle et al., Textbook of Cardiovascular Medicine, E. J. Topol, ed. (Philadelphia, Pa., Lippincott Williams & Williams) (2002). Atherosclerosis is an inflammatory process by which the intima becomes thickened due to lipid rich gruel, an aggregation of macrophages and T-lymphocytes, which eventually forms a fibrous plaque that protrudes into the lumen of the vessel hampering blood flow. It is the principal cause of myocardial and cerebrovascular infarction in hypertensive patients (leading causes of death in the Western world), as well as gangrene in the lower extremities of diabetic patients. See Ross, Nature 362:801-809 (1993).

Nogo-B and fragments that retain Nogo-B activity vis a vis endothelial cells and vascular smooth muscle cells, i.e., fragments that promote endothelial cell adhesion, spreading and/or migration, that inhibit vascular smooth muscle cell migration, that promote angiogenesis and/or inhibit or reduce neointima formation in a blood vessel are useful to maintain vascular health and integrity, repair vascular injury, and promote vascular proliferation. Accordingly, in another aspect, the invention provides a method for promoting angiogenesis in a subject in need thereof. Enhanced angiogenesis is desired, for example, in connection with wound healing, in diabetes that is characterized by peripheral vascular disease (i.e., insufficient peripheral vasculature), in coronary artery disease (to by-pass blockages in blood vessels).

According to another aspect of the invention, Nogo-B is shown to prevent or reduce undesirable vascular remodeling such as neo-intima formation in injured blood vessels. Such pathological intima formation narrows the lumen of the blood vessel and may even cause complete occlusion of the vessel. Such vascular neo-intima formation often follows procedures such as angioplasty, mycardial infarction and in tissue and organ transplantation. As shown herein, injury to blood vessels leads to decreased levels of Nogo-B in the blood vessel cells. Also as shown herein, contacting such blood vessels with Nogo-B promotes healing and reduced or inhibited neointima formation. Nogo-B and biologically active fragments thereof are useful to treat conditions including hypertension, restinosis, transplant vasculopathy, arteriosclerosis, ischemia, hypertension, pulmonary hypertension, asthma, vascular infarctions including myocardial infarction, and other conditions characterized by Nogo-B mediated undesirable vascular remodeling.

In some conditions, it is desirable to inhibit or suppress angiogenesis. In such conditions, it would be desirable to inhibit Nogo-B mediated effects on blood vessels either by inhibiting the expression level or one or more biological activities of Nogo-B. Accordingly, in a further aspect, the invention provides a Nogo-B antagonist. Antagonists may include any Nogo-B binding partner, preferably a binding partner that specifically binds Nogo-B and inhibits one or more Nogo-B activities. Antagonist binding partners include but are not limited to antibodies, small molecules, peptides, and the like. Alternatively, it may be desirable to reduce expression of Nogo-B at the level of transcription, translation or post-translation processing. Such inhibition of Nogo-B expression may be accomplished by any means known in the art, including but not limited to short interfering RNA (siRNA), antisense nucleic acids and/or ribozymes. In accordance with the present invention, compositions comprising Nogo-B or a biologically active fragment thereof, such as Am-Nogo-B, may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of therapeutic proteins are well known in the art.

The precise dose will depend upon a number of factors, including whether the composition is for diagnosis or for treatment, the size and location of the area to be treated, the precise nature of the therapeutic compound (e.g. whole protein, fragment or fusion protein), and the nature of any detectable label or other molecule attached to the compound. A typical dose will be in the range 100 µg to 1 gm for systemic applications, and 1 µg to 1 mg for topical applications. This is a dose for a single treatment of an adult patient, which may be proportionally adjusted for children and infants, and also adjusted for other formats in proportion to molecular weight. Treatments may be repeated at daily, twice-weekly, weekly or monthly intervals, at the discretion of the physician. In preferred embodiments of the present invention, treatment is periodic, and the period between administrations is about two weeks or more, preferably about three weeks or more, more preferably about four weeks or more, or about once a month.

The composition comprising Nogo-B or a Nogo-B antagonist may be administered via an oral, mucosal, buccal, intranasal, inhalable, intravenous, subcutaneous, intramuscular, parenteral, intratumor, transdermal or topical route. The composition can also be administered continuously via a minipump. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York, 1978).

In certain embodiments, the Nogo-B composition can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the active compound can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds also can be incorporated into the compositions. In certain embodiments, Nogo-B is co-formulated with and/or co-administered with one or more additional therapeutic agents. Throughout this specification and claims, the word "comprise," or variations such as "comprises" or "comprising," will be understood to imply the inclusion of a stated integer or group of integers but not the exclusion of any other integer or group of integers.

EXAMPLES

In order that this invention may be better understood, the following examples are set forth. These examples are for the purpose of illustration only and are not to be construed as limiting the scope of the invention in any manner.

Example 1

Isolation of CEM/LR and Identification of Nogo-B in CEM/LR Domains of Endothelial Cells Within endothelial cells, it is proposed that localization of signaling molecules to CEM/LR is necessary for angiogenic growth factor signal transduction. The following example identifies Nogo-B in CEM/LR domains of EA.hy.926 s endothelial cells.

Materials and Methods

Isolation of CEM/LR and Proteomic Analysis:

Cell Culture

EA.hy.926 cells were grown to 70% confluency in high glucose DMEM medium containing 10% (v/v) fetal calf serum (FCS; Invitrogen, Burlingame, Calif.), L-glutamine (2 millimolar (mM); Invitrogen), penicillin (100 units/milliliter (ml); Invitrogen), streptomycin (100 mg/ml; Invitrogen). Media for EA.hy.926 cells also contains hypoxanthine (100 micromolar (µM)), aminopterin (0.4 µM), and thymidine (16 µM) supplement (HAT; Sigma, St. Louis, Mo.). For proteomic analysis, cells were grown to 70-80% confluency.

Isolation of CEM/Lipid Rafts (LR) for MALDI-ReTOF

CEM/LR from 25 each 150 millimeter (mm) dishes of proliferating EA.hy.926 cells were prepared using sodium carbonate/sucrose density gradient fractionation, as follows: EA.hy.926 cells were lysed on ice in 500 mM $Na_2CO_3$, pH 11. Lysate was then sonicated 3 times for 20 seconds at a low output and mixed in a 1:1 ratio with 85% sucrose prepared in MBS (25 mM MES, pH 6.5, 150 mM NaCl). A discontinuous sucrose gradient comprising 6 ml 30% and 2 ml 5% sucrose (containing MBS and 250 mM $Na_2CO_3$, pH 11) was loaded on top of sample. Gradients were spun at 35,000 rpm in SW-40 rotor (Beckman Instruments, Palo Alto, Calif.) for 16-20 hours at 4° C. 1 milliliter (ml) fractions were collected from top to yield a total of 12 fractions. For further purification, the light-scattering fraction(s) corresponding to CEM/LR was reprocessed on a discontinuous sucrose gradient. To concentrate the CEM/LR, the sucrose was diluted out with water and samples were spun at 35,000 rpm in SW-40 for 1-2 hours. The pellet was then resuspended in 2× Lamelli sample buffer and boiled for SDS-PAGE. For confirmation of protein localization to CEM, 150 mm dishes of EA.hy.926 cells were plated and processed as above.

Western Blot Analysis and Antibodies

After sodium carbonate/sucrose density gradient fractionation, 25 microliters (µl) of each fraction (nos. 1-12) were electrophoresed using SDS-PAGE on 10% gels. Proteins were transferred onto nitrocellulose membranes at 4 degrees Celsius (° C.) using Towbins buffer (125 mM Tris-HCl, 95 mM glycine) with 20% methanol. Membranes were stained with Ponceau S to visualize protein bands and washed with Tris buffered saline (TBS; 10 mM Tris, pH 7.4, 150 mM NaCl). Nitrocellulose membranes were then blocked for at least 1 hour in TBS containing 5% powdered milk and incubated with appropriate antibody for greater than 1 hour. Membranes were extensively washed with TBS plus 0.001% Tween 20 (TBST) and then incubated for 1 hour with complementary horseradish peroxidase conjugated secondary antibody (Amersham, Piscataway, N.J.). Once again membranes were extensively washed in TBST and developed using enhanced chemiluminescence substrate (ECL, Amersham). Some membranes were stripped for 15 minutes at 50° C. in buffer containing 2% (v/v) SDS, 62.5 mM Tris-HCl, pH 6.7, and 100 mM β-mercaptoethanol to be re-probed with other antibodies. To confirm separation of CEM/LR from other organelles and later the localization of Nogo-B to CEM/LR, Western blot analysis of equal volumes from fractions 1-12 was performed, using the following antibodies as markers for different subcellular locations: anti-caveolin-1 (indicates localization to CEM/LR (fractions 2-4); anti-angiotensin converting enzyme (ACE; mouse mAb at 1 µg/ml; QED Bioscience, San Diego, Calif.) (indicates localization to bulk plasma membranes(fractions 9-12), and anti-beta-COP (β-COP; rabbit pAb 1:1000; Affinity Bioreagents, Golden, Colo.) (indicates localization to Golgi bodies (fractions 9-12). In this way, the cellular fraction containing CEM/LR was identified and isolated for use in proteomic analysis by MALDI-ReTOF (see below). The total protein content of the isolated CEM/LR was then electrophoresed on a SDS-PAGE gradient gel and visualized using Coomassie Blue staining (50% Methanol (J.T. Baker; Phillipsburg, N.J.), 0.05% Coomassie brilliant blue (Bio-Rad), and 10% glacial acetic acid (J.T. Baker) in water) to visualize proteins. Prominent bands were excised from the gel slab and processed for MALDI-ReTOF mass spectroscopy.

MALDI-ReTOF Mass Spectroscopy

Concentrated CEM were run on a 5-20% gradient SDS-PAGE and stained with Coomassie blue. The thirty-most prominent, gel-resolved proteins were excised, digested with trypsin, and partially fractionated. The resulting peptide mixtures were analyzed by matrix-assisted laser-desorption/ionization reflectron time-of-flight (MALDI-reTOF) mass spectrometry (MS) (Reflex III; BRUKER Daltonics, Bremen, Germany) and an electrospray ionization (ESI) triple quadrupole MS/MS instrument (API300; ABI/MDS SCIEX, Thornhill, Canada) modified with an ultra-fine ionization source. Selected precursor or fragment ion masses from the MALDI-reTOF MS or nanoelectrospray (NanoES)-MS/MS spectra were taken to search a protein non-redundant database ('NR'; National Center for Biotechnology Information, Bethesda, Md.). MS/MS spectra also were inspected for y" ion series to compare with the computer-generated fragment ion series of the predicted tryptic peptides. In this way, one of the proteins identified through mass spectroscopy using MALD-ReTOF was Nogo-B.

Expression of Nogo-B mRNA and Nogo-B in Endothelial Cells and Vascular Smooth Muscle Cells Cell culture—EA.hy.926 cells were cultured as previously as described above. Human umbilical vein endothelial cells (HUVEC) were cultured in M199 medium containing 20% (v/v) fetal calf serum (FCS) and endothelial cell growth supplement (ECGS; 50 micrograms per milliliter (µg/ml); BD Biosciences). COS-7 cells were cultured in high glucose DMEM with 10% (v/v) FCS. Human aortic vascular smooth muscle cells (HAVSMC) cultured in M199 medium with 20% FCS. All media were supplemented with 2 mM L-glutamine, 100 units/ml penicillin, and 100 mg/ml streptomycin.

Reverse Transcriptase Polymerase Chain Reaction. (RT-PCR)

Total cellular RNA was isolated using RNEasy Kit (Qiagen, Valencia, Calif.). For cloning of Nogo-B, first-strand cDNA was generated using Superscript II (Invitrogen) from 4 µg total RNA according to manufacturer's instructions. The full length coding sequence of Nogo-B was amplified with HA tag added, ligated into pcDNA3 and sequenced. To determine the levels of various transcripts, RT-PCR was performed using 200 ng RNA and primers specific for Nogo-A, Nogo-B, Nogo-B2, Nogo-C, and beta-actin (β-actin; Invitrogen). 10 ng Nogo-B-HA in pcdna3 and Nogo-A in pcdna3.1-Myc-His plasmid were used as controls.

Western Blot Analysis

COS-7 cells plated in 60 mm dish and grown to 90% confluency were transfected with 2 µg Nogo-B-HA in pcdna3 and Nogo-A in pcdna3.1-Myc-His plasmids using Lipofectamine 2000 (Invitrogen) to serve as controls. HUVEC, HAVSMC, and EA.hy.926 cells were grown to confluency in 100 mm dishes, rinsed with PBS, and lysed in a modified RIPA buffer (50 mM Tris-HCl, pH 7.4, 1% Nonidet-40, 0.1 mM EDTA, 0.1 mM EGTA, 0.1% SDS, 0.1% deoxycholic acid, 1 mM Pefabloc, and 15 mg protease inhibitor cocktail tablet (Roche)). 20 µg protein lysate was loaded onto a 10% SDS-PAGE gel for electrophoreses. After transferring onto nitrocellulose membrane as described previously, membranes were blocked with 0.1% Casein in TBS for at least 1 hour. Expression of Nogo was detected using anti-Nogo (1-18) (goat pAb, 1:1000; Santa Cruz Biotechnology), followed by Alexa680 conjugated secondary antibody (Molecular Probes; Eugene, Oreg.). Anti-hsp90 (BD Biosciences Transduction Labs) followed by IRDye800 conjugated secondary antibody (Rockland Immunochemicals; Gilbertsville, Pa.) was used to control for loading. After incubation with either primary or secondary antibody, membranes were extensively washed with TBS plus 0.001% Tween 20 (TBST) prior to the next step. Membranes were then scanned using Li-Cor Odyssey Infrared Imaging System (Li-Cor Biosciences; Lincoln, NE).

Isolation of CEM/LR to Confirm Localization of Nogo-B

CEM/LR from a 150 mM dish of EA.hy.926 cells was prepared using a sodium carbonate/sucrose density gradient fractionation as described above. 1 ml fractions were collected from the top to yield a total of 12 fractions.

Isolation of Plasma Membrane CEM/LR

EA.hy.926 cells were plated onto 10 150 mM dishes and grown to confluency. Cells were collected in 50 mM Tris pH 9.6, 250 mM sucrose, 10 mM NaCl, and 5 mM $MgCl_2$ and pelleted at 1000 rpm for 5 minutes at 4° C. Cells were resuspended in 6 ml hypotonic buffer (50 mM Tris pH 9.6, 10 mM NaCl, and 5 mM $MgCl_2$), allowed to swell for 10 minutes at 4° C., and homogenized with 20 strokes in Dounce homogenizer. A 1:1 ratio of hypertonic buffer (50 mM Tris pH 9.6, 500 mM sucrose, 10 mM NaCl, and 5 mM $MgCl_2$) was added to homogenate and spun twice at 2500×g to remove nuclei and unbroken cells. This supernatant, also known as the starting material (SM), was spun at 7,500 rpm for 15 minutes at 4° C. in SW-40 rotor to pellet plasma membrane sheets (PM). PM was resuspended in 500 mM sodium carbonate, pH 11 and processed as above to isolate CEM/LR (PC).

Results

Nogo-A, Nogo-B and Nogo-B2 mRNA were identified in both EA.hy.926 and HUVEC cells. See FIG. 1.

Figure 2:
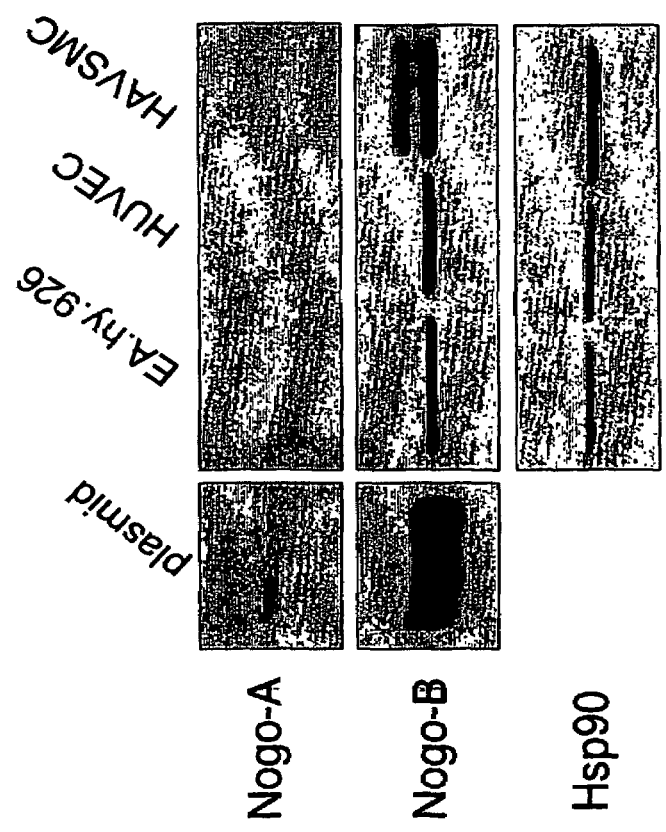
FIG. 2. Expression of Nogo-B protein in vascular cells.

In contrast, Western blot analysis using an antibody that recognizes amino acids 1-18 common to the amino terminus of both Nogo-A and -B [anti-Nogo (1-18)] identifies only endogenously expressed Nogo-B protein in both EA.hy926 cells and HUVEC cells. To control for antibody specificity, lysates were taken from COS-7 cells transfected with plasmids encoding either Nogo-A or Nogo-B. Protein expression of Nogo-A was found only in cells transfected with the Nogo-A cDNA. See FIG. 2.

Western blot analysis of equal volume from fractions demonstrated the localization of Nogo-B to light fractions corresponding to CEM/LR (fractions 2-4). Isolation of CEM/LR is marked by the relative enrichment of caveolin-1 in light fractions versus heavy fractions (9-12) which contained ACE, a marker of bulk plasma membranes, and β-COP, a Golgi body marker (data not shown).

Example 2

Analysis of the Effect of Nogo-B on Vascular Cell Function: Cell Spreading

Because of the extracellular orientation of the N-terminus of Nogo-B, this domain was analyzed to determine its effects on vascular cells.

Methods and Materials

Cell culture
EA.hy.926 and HUVEC cells were cultured as previously described in Example 1.

Expression Vectors
GST-Am-Nogo B was generated by ligating cDNA encoding amino acids 1-200 of Nogo-B into pGEX4T-1 (Amersham). AP-Am-Nogo B was generated by ligating above mentioned residues into pAP6.

Purification of GST Constructs
The recombinant fusion proteins were expressed in Escherichia coli BL-21 Codon Plus (Stratagene, La Jolla, Calif.) using 0.5 mM IPTG induction for two hours and bacterial cell lysates were prepared in STE buffer (150 mM NaCl, 7.5 mM Tris, pH 8.0, 3 mM EDTA) with 100 µg/ml lysozyme, 5 mM DTT, 1 mM Pefabloc, and 15 mg protease inhibitor cocktail tablet. The lysate was adsorbed to 3 ml glutathione-sepharose 4B gel (Amersham) previously equilibrated with STE. The gel was extensively washed with STE and bound proteins were eluted with STE containing 15 mM reduced glutathione.

Cell Spreading Assays
125 picomoles (pmol) GST, GST-Am-Nogo-B, GST-Nogo-66, in a final volume of 25 µl, or 25 PBS (protein free control) was added to 0.02% Poly-L-lysine coated 12 mm coverslips in a final volume of 25 µl and let dry overnight in a 24 well plate. 50,000 EA.hy.926 or COS-7 cells were then added and allowed to adhere onto coverslips for 2 hours prior to fixation with 3.7% formaldehyde for 10 minutes at room temperature. Cells were permeabilized with 0.1% Triton-X 100 for 5 minutes and stained with Alexa 594 conjugated phalloidin (1:50; Molecular Probes) for 1 hour. Coverslips were mounted as described in Chapter 3. Between 150 and 200 cells were counted per coverslip at 400× magnification. The number of spread cells relative to the total number of cells per field was counted to calculate percent spreading.

Results

Figure 3:
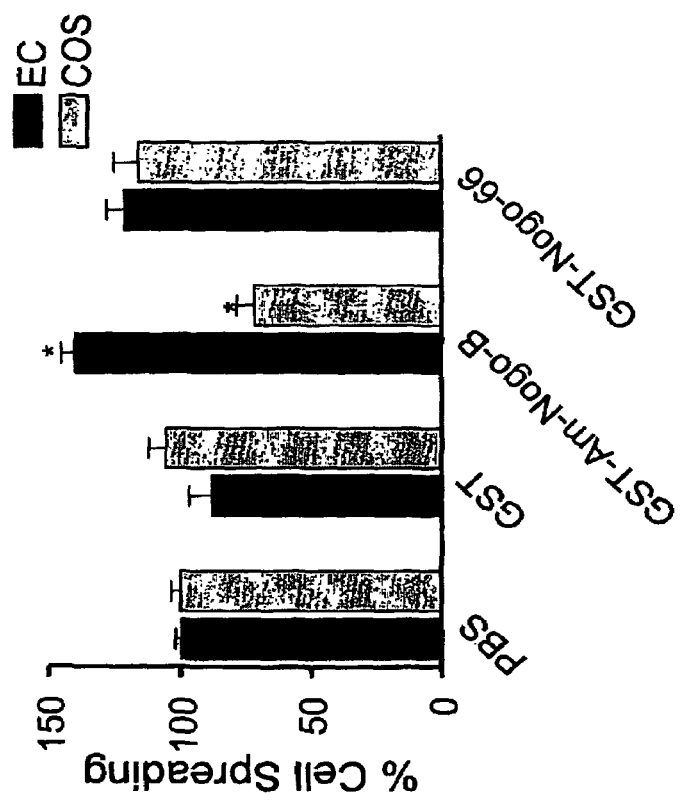
FIG. 3. GST Am-Nogo-B promotes endothelial cell, but not COS-7 cell spreading.

GST-Am-Nogo-B promotes endothelial cell (EA.hy.926 cells) spreading but not COS cell spreading. GST-Nogo-66 has no significant effect on the spreading of either cell type. Neither PBS or GST alone has any effect on cell spreading. See FIG. 3.

Example 3

Analysis of the Effect of Nogo-B on Vascular Cell Function: Cell Adhesion

Because of the extracellular orientation of the N-terminus of Nogo-B, this domain was analyzed to determine its effects on vascular cells.

Methods and Materials

Cell Culture
EA.hy.926 and HUVEC cells were cultured as previously described in Example 1, above.

Expression Vectors
GST-Am-Nogo-B was generated as in Example 2, above.

Purification of GST Constructs
GST-Am-Nogo-B was purified as in Example 2, above.

Cell Adhesion Assays
Adhesion experiments were performed as follows: Titerek cell culture plates were coated with 0.02% poly-L-lysine. 25 picomoles (pmol) of GST or GST-Am-Nogo-B were then added to the plates, and the plates were allowed to dry overnight. Phosphate-buffered saline (PBS) was used as a protein-free control on a third set of slide covers. For analysis of dose-dependant responses, 2.5-250 pmol GST or GST-Am-Nogo-B were coated into each well. 40,000 EA.hy.926 or HUVEC cells were plated into each well and let adhere for 1 hour prior to fixation with 2% paraformaldehyde/PBS and staining with 0.1% Crystal violet for at least 1 hour. For quantitation, plates were rinsed extensively with water, stain was extracted with 1% N-lauryl sarcosine. Adherent cells were measured using 0.1% crystal violet which is a dye used to stain cells. Because non-adherent cells were rinsed off prior to staining, only adherent cells were stained. The crystal violet dye from adherent cells in each well were solublized with the detergent N-lauryl sarcosine. The optimal wavelength to measure the intensity of crystal violet is 590 nm on the spectrophotometer. Therefore, the amount of adhesion was determined by measuring the optical density (OD) at a wavelength of 590 nm ($OD_{590}$).

Results

Figure 4:
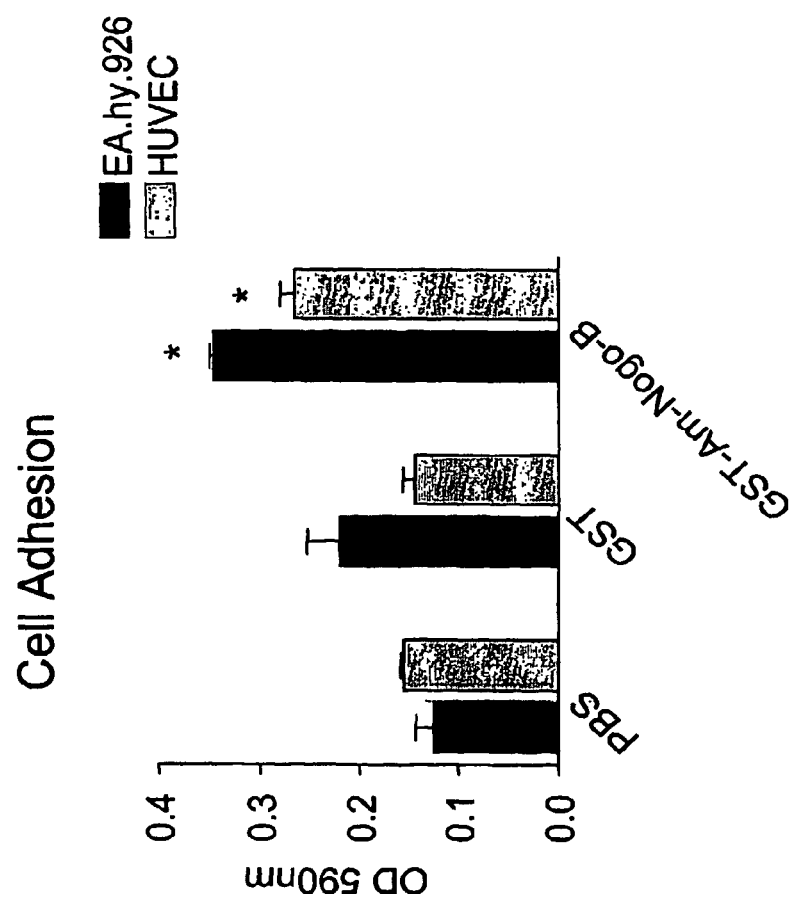
FIG. 4.

GST-Am-Nogo-B promotes adhesion of endothelial cell (both EA.hy.926 and HUVEC cells). Neither PBS or GST alone has any effect on cell spreading. See FIG. 4.

Figure 5:
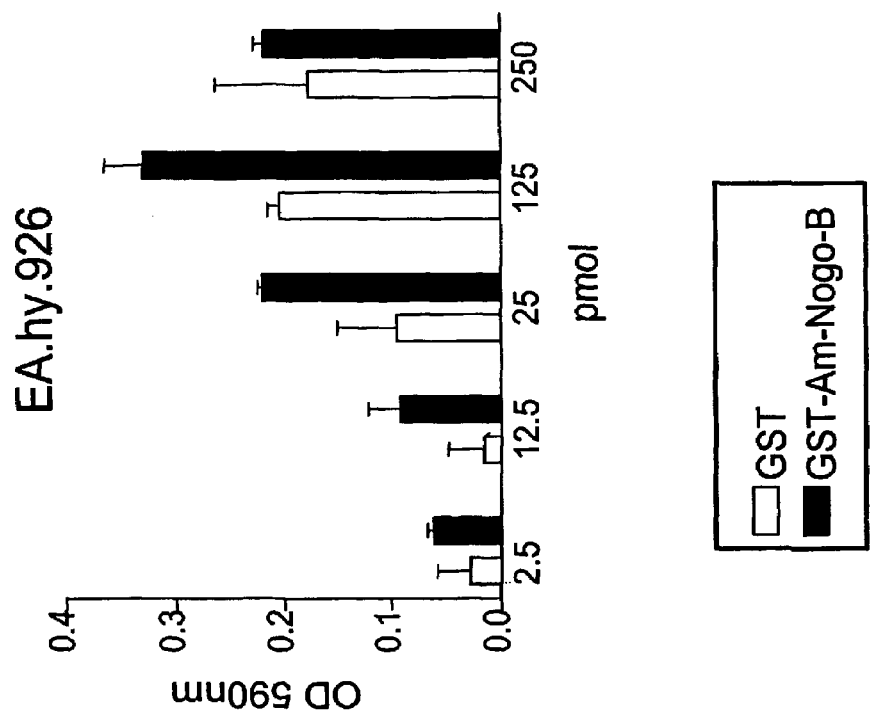
FIG. 5.

GST-Am-Nogo-B promotes adhesion of EA.hy.926 cells in a dose-dependent manner. GST alone has no effect on cell spreading. See FIG. 5.

Example 4

Analysis of the Effect of Nogo-B on Vascular Cell Function: Cell Migration

Because of the extracellular orientation of the N-terminus of Nogo-B, this domain was analyzed to determine its effects on vascular cells.

Methods and Materials

Cell Culture
EA.hy.926 and HUVEC cells were cultured as previously described in Example 1, above.

Expression Vectors

GST-Am-Nogo-B was generated as in Example 2, above.

Purification of GST Constructs

GST-Am-Nogo-B was purified as in Example 2, above.

Cell Migration Assays

A modified Boyden chamber with Costar transwell inserts (Corning Inc., Acton, Mass.) was used in this example. The transwell inserts were coated with a solution of 0.1% gelatin (Sigma, St. Louis, Mo.) in PBS at 4° C. overnight and then air-dried. For endothelial cells, vascular endothelial growth factor (VEGF; used as a positive control) at a concentration of 1.1 nM and various concentrations (1 nM, 10 nM and 100 nM) of GST-Am-Nogo-B were dissolved in Medium 199 (Earle's salts, L-glutamine, and 2,200 mg/L sodium bicarbonate (Gibco)) containing 0.1% bovine serum albumin (BSA) and added to the lower chambers of the Boyden apparatus. HUVEC cells ($2\times10^5$ cells) in 100 µl Medium 199 containing 0.1% BSA were added to the upper chambers and incubated for 5 hours. After incubation, cells on both sides of the membranes (i.e., the transwell inserts) were fixed and stained with Diff-Quik staining kit (Baxter Healthcare Corp, Dade Division, Miami, Fla.). The average number of cells that had migrated to the lower chamber were counted from five randomly chosen high power (×400 magnification) fields.

Results

Figure 6:
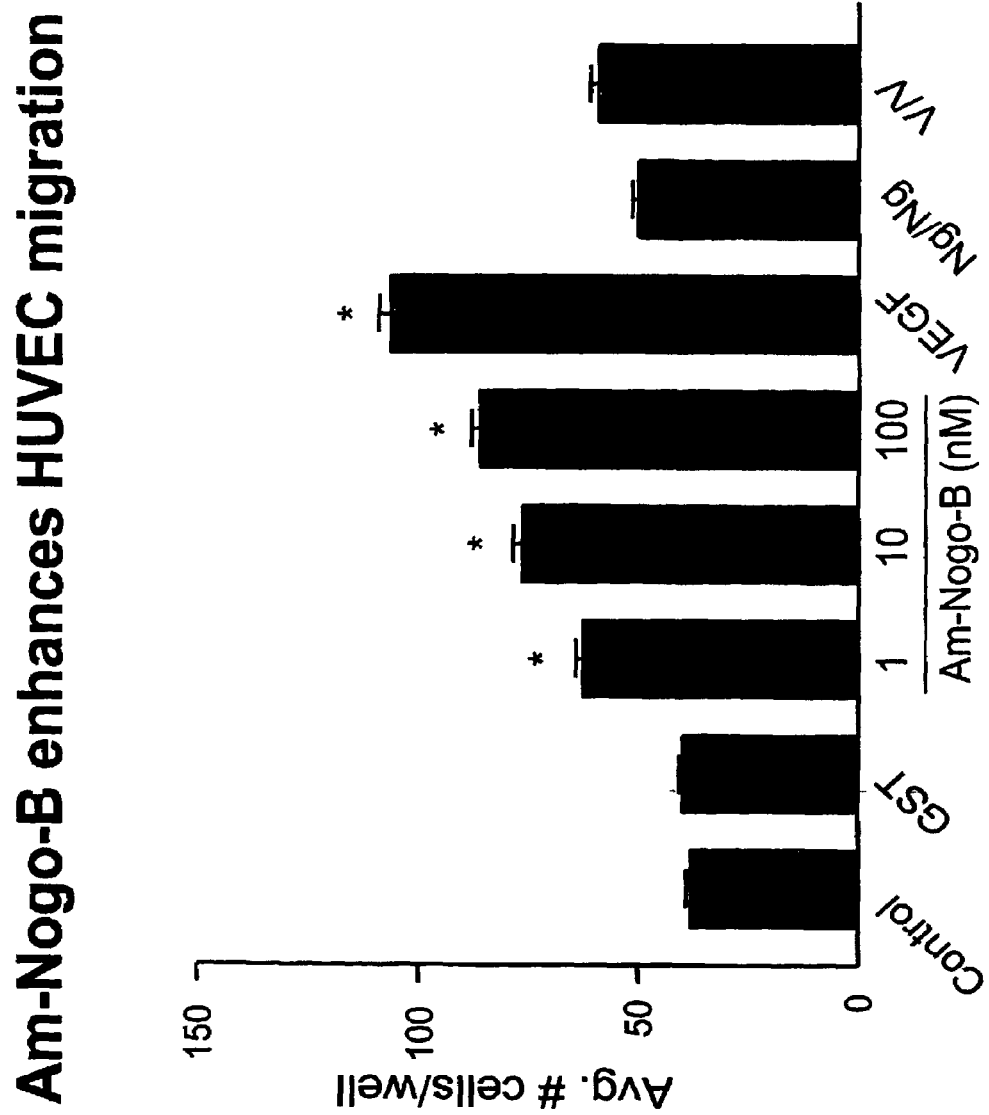
FIG. 6. GST-Am-Nogo is a chemoattractant for HUVEC cells.

GST-Am-Nogo-B, but not GST alone, increased endothelial cell (HUVEC) migration in a dose-dependant manner. In other words, Nogo-B is a chemoattractant for endothelial cells. This procedure was repeated 3 times with similar results. See FIG. 6.

Example 5

Determination of the Presence of Nogo-B in Intact Blood Vessels

Materials and Methods

Reverse Transcriptase Polymerase Chain Reaction (RT-PCR)

RT-PCR analysis was used to detect Nogo messenger RNA (mRNA) in murine brain and in various murine blood vessels: femoral artery, carotid artery, thoracic aorta and abdominal aorta. Total RNA from tissue was isolated using RNEasy Kit (Qiagen, Valencia, Calif.). To determine the levels of various transcripts, RT-PCR was performed using 100 nanograms (ng) of RNA and primers specific for Nogo-A, Nogo-B, Nogo-B2, Nogo-C, and β-actin (Invitrogen).

After RT-PCR was complete, the resulting mRNA was loaded onto an agarose gel containing ethidium bromide and electrophoresed. The RNA bands were then visualized under ultraviolet (uV) light. Only bands representing RNA that had been amplified (by RT-PCR) from cellular RNA can be visualized on the gel slab.

Preparation of Mice Tissue Samples for Western blot Analysis of Vessels

Upon sacrifice, C57BL/6J or Nogo-A/B (−/−) mice were perfused with PBS; brain and blood vessels were excised and snap frozen in liquid nitrogen. Tissue was crushed on dry ice and homogenized in modified RIPA buffer. 50 µg protein lysate was loaded onto a 10% SDS-PAGE gel for electrophoreses. After transferring onto nitrocellulose membrane, as described previously membranes were then blocked for at least 1 hour in TBS containing 5% powdered milk.

Western Blot Analysis of Vessels

Western Blot Analysis was used to identify endogenously expressed Nogo proteins in murine brain and in various murine blood vessels: femoral artery, carotid artery, thoracic aorta and abdominal aorta. Expression of Nogo was detected using anti-Nogo 1-18 (Santa Cruz Biotechnology, Santa Cruz, Calif.), an antibody that recognizes amino acids 1-18 of the N-terminus of both Nogo-A and Nogo-B or an antibody, anti-Nogo-A, that recognizes only Nogo-A. As antibody (Ab) controls, COS-7 cells were transfected with either a plasmid encoding Nogo-B (pcdna3NogoB) or a plasmid encoding Nogo-A (pcdna3.1NgA-MycHis), using Lipofectamine 2000 (Invitrogen, Burlingame, Calif.) to accomplish the transfection. Anti-β-actin (Sigma, St. Louis, Mo.) was used as a loading control.

Results

Figure 7:
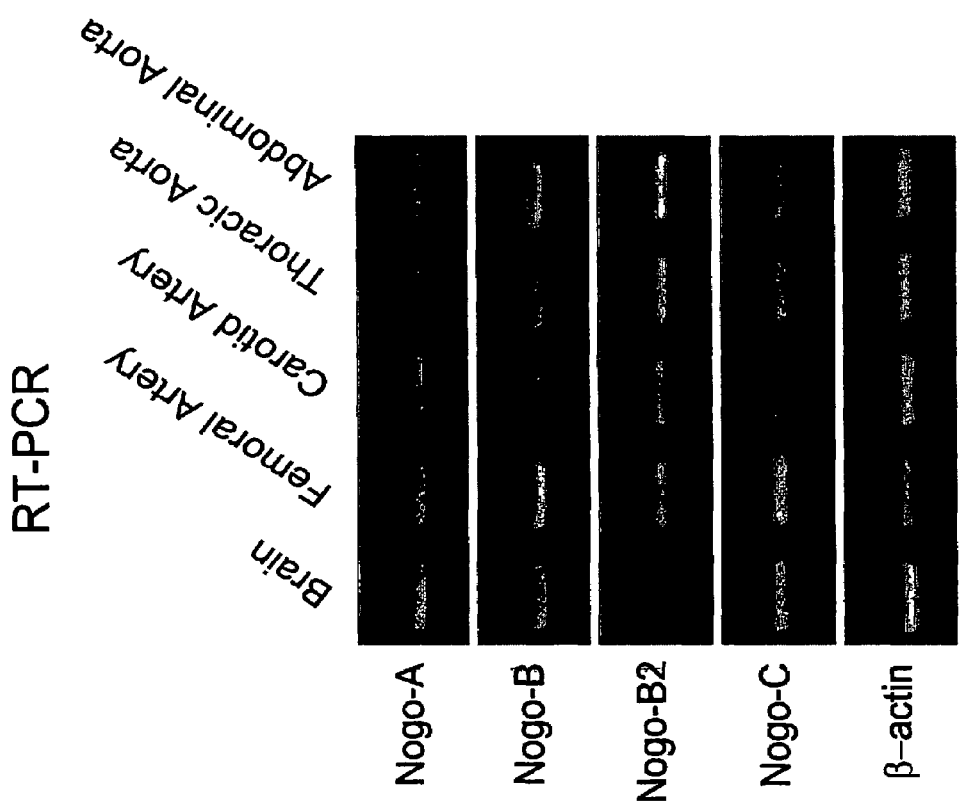
FIG. 7. Identification of Nogo mRNA in murine brain and in various murine blood vessels: femoral artery, carotid artery, thoracic aorta and abdominal aorta.

Nogo-A, Nogo-B, Nogo-B2 and Nogo-C mRNA were identified in murine brain and in murine femoral arteries, carotid arteries, thoracic aortas and abdominal aortas. See FIG. 7.

Figure 8:
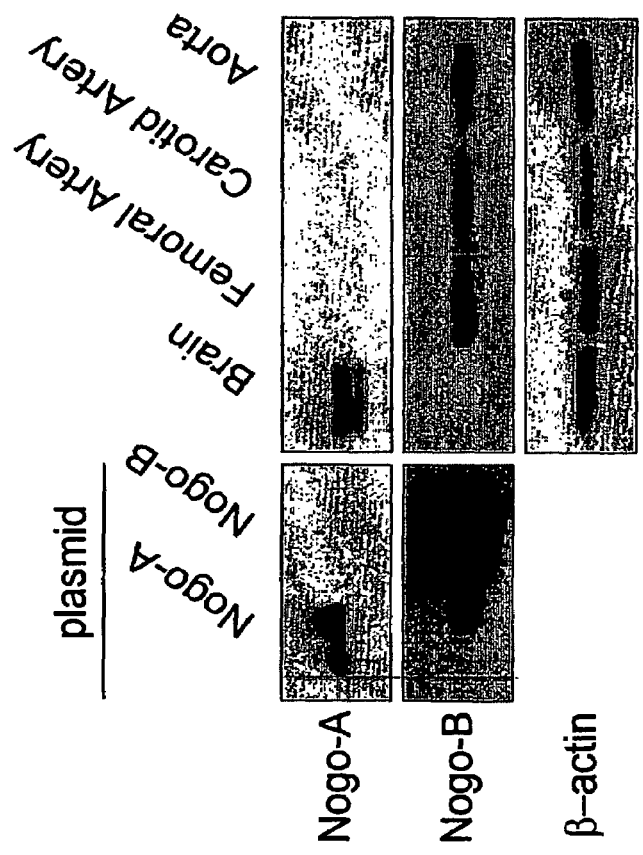
FIG. 8. Expression of Nogo-B protein in murine brain and in various murine blood vessels: femoral artery, and carotid artery, and aorta.

In contrast, Western blotting detected only Nogo-B protein in murine aortas, femoral arteries and carotid arteries and only Nogo-A protein in murine brains. See FIG. 8.

Example 6

Determination of the Tissue Distribution of Nogo-A and Nogo-B in vivo in Mice

Nogo-A/Nogo-B-deficient mice were used to track the endogenous expression of Nogo-A and Nogo-B in brain and aorta of mice. See Kim et al., Neuron 38:187-199 (2003) ("Kim")

Materials and Methods

Nogo-A/Nogo-B Deficient Mice

A β-galactosidase gene was inserted in-frame into the Nogo-A/Nogo-B encoding locus to generate Nogo-A/Nogo-B-deficient mice. In this way, expression of Nogo-A and/or Nogo-B was coupled with expression of β-galactosidase. The knockout of Nogo-B in the vessels of these mice was confirmed by performing a Western blot analysis using lysates from murine brain, and both wild-type and Nogo-A/Nogo-B-deficient (−/−) aortas.

Also, in these mice, X-gal staining to assess beta-galactosidase activity was used to track endogenous expression of the nogo gene products Nogo-A and Nogo-B in a murine (Nogo-A/Nogo-B-deficient, as described above) artery/vein pair and a murine aorta.

C57BL/6J mice were used as a wild-type model (Nogo-A/Nogo-B (+/+).

Western Blot Analysis of Vessels

Upon sacrifice, C57BL/6J (wild-type) or Nogo-A/B (−/−) mice were perfused with PBS; brains and aortas were excised and snap frozen in liquid nitrogen. Tissue was crushed on dry ice and homogenized in modified RIPA buffer. 50 µg protein lysate was loaded onto a 10% SDS-PAGE gel for electrophoreses. After transferring onto nitrocellulose membrane, as described previously membranes were then blocked for at least 1 hour in TBS containing 5% powdered milk. Expression of Nogo was detected using anti-Nogo (1-18) (Santa Cruz Biotechnology) or anti-Nogo-A (rabbit pAb, 1:5000); according to Wang et al., J. Neurosci. 22:5505-5515 (2002)

("Wang"). Anti-p-actin (Sigma) was used to control for loading. Membranes were extensively washed with TBST and then incubated for 1 hour with complementary horseradish peroxidase conjugated secondary antibody (Amersham).

X-gal staining

Upon sacrifice, Nogo A/B (+/−) mice were perfused with PBS and perfusion fixed with 2% paraformaldehyde in PBS. Tissues were excised and stained overnight at 37° C. with 1 mg/ml X-gal (American Bioanalytical; Natick, Mass.) in X-gal Reaction Buffer (5 mM potassium ferrocyanide, 5 mM potassium ferricyanide, and 2 mM $MgCl_2$). Vessels were dehydrated in 15% sucrose at 4° C. and embedded in OCT. Cryostat frozen sections were obtained for the femoral and aorta (5 μm and 10 μm respectively). Whole mount pictures of tissues were taken on a camera mounted on a dissecting scope prior to embedding in paraffin for 5 μm sections counterstained with Eosin Y by the Yale Research Histology Lab. For lung sections Nogo-A/B (−/−) mice were used.

Results

Figure 9:
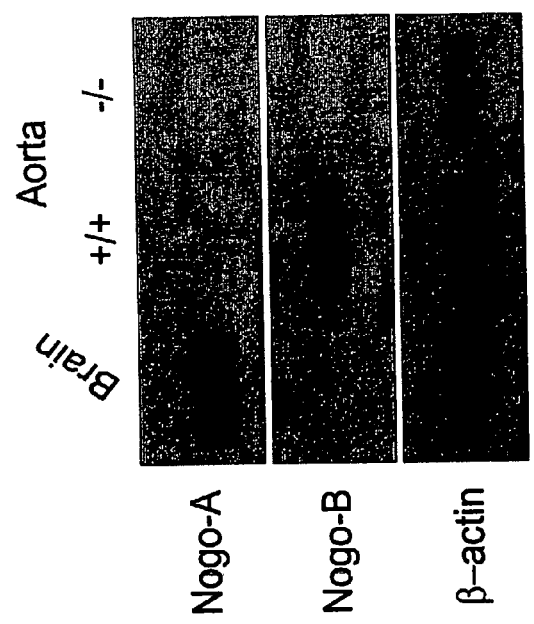
FIG. 9. Expression of Nogo-A and Nogo-B protein in Nogo-A/B (−/−) mice. A β-galactosidase gene was inserted in-frame into the Nogo-A/Nogo-B encoding locus to generate Nogo-A/Nogo-B-deficient mice, and used to track endogenous expression of Nogo-A and Nogo-B in the brains and aortas of mice.

Nogo-B, but not Nogo-A, is endogenously expressed in murine wild-type aortas. Conversely, Nogo-A, but not Nogo-B, is endogenously expressed in murine brains. See FIG. 9.

Example 7

Determination of the Extent of Vascular Injury in Nogo-A/B Knockout Mice

To assess the role of Nogo-B in vessel remodeling wire injury of the femoral artery was used as a model of luminal remodeling and neointima formation. In this example, a guide wire is used to denude the endothelium and cause trauma to the media.

Methods and Materials

Mice Models

Nogo-A/Nogo-B-deficient were as described in Example 6, above. C57BL/6J mice were used as a wild-type model (Nogo-A/Nogo-B (+/+), as in Example 6, above. Nogo-A/Nogo-B (−/+) mice were back crossed 7 generations onto a C57BL/6J background and used to generate wild-type (WT) and Nogo-A/B (−/−) littermate mice.

Femoral Artery Injury and Adenoviral Transduction

Nogo-A/Nogo-B (−/+) mice were back crossed 7 generations onto a C57BL/6J background and used to generate wild-type (WT) and Nogo-A/B (−/−) littermate mice. Male, 8-10 week old Nogo-A/B (−/−) or WT littermate mice were anesthetized with ketamine/xylazine (79.5 mg/kg ketamine, 9.1 mg/kg xylazine) and femoral arterial injury, adenoviral infection and morphometry were performed. Injured femoral arteries were collected 3 weeks after surgery.

Histology and Immunohistochemistry

After sacrifice, tissue was perfusion fixed with 4% paraformaldehyde in PBS, PH 7.4 at 100 mm Hg pressure or fresh femoral arteries were taken and embedded in O.C.T (Tissue-Tek Elkhart, Ind.). Cryosections (5 μm) of arteries were obtained for hematoxylin/eosin and elastic staining. For immunohistochemistry, sections were incubated with anti-CD31/PECAM (1:500 rat mAb, Pharmigen), biotin conjugated anti-CD45 (1:100 rat mAb, Pharmigen), or horseradish peroxidase conjugated anti-smooth muscle actin (SMA, DAKO, Glostrup, Denmark). Anti-CD31 and CD45 were followed by biotin-anti-rat (1:200, Pharmigen) and Vectastain® ABC (Vector Labs). Staining was developed using NovaRed™ peroxidase substrate kit (Vector Labs). For immunofluorescent staining, sections were incubated with anti-Nogo (1-18) (1:50), followed by Alexa594 conjugated secondary antibody (1:200; Molecular Probes) or anti-HA (1:50), followed by Alexa594 conjugated secondary antibody (1:200, Molecular Probes).

Protocol for BrdU Labeling and Staining of Mice Arteries

Mice were injected sub-cutaneously with 25 mg/kg body weight BrdU (Sigma) at a concentration of 5 mg/ml in saline every day for 3-7 days prior to sacrifice. 12-24 hours before sacrifice, mice were injected IP with one dose of 30 mg/kg body weight. Upon sacrifice, mice were perfused with PBS and non-fixed femoral arteries were embedded in O.C.T. (Tissue-Tek Elkhart, Ind.). Cryosections (5 μm) of arteries were obtained for immunohistochemistry. Slides were allowed to airdry for 1 hour at room temperature prior to fixation ice cold acetone for 15 min. Slides were then washed in PBS 2 times 5 minutes and endogenous peroxidase activity was blocked by incubation 0.3% $H_2O_2$/PBS for 10 minutes. Sections were again washed in PBS 2 times 5 minutes and boiled for 10 minutes in 10 mM citrate buffer, pH 6.0 @ 95° C. for antigen retrieval. Artery sections were blocked in 10% serum for 1 hour at room temperature and then incubated with anti-BrdU (1:300 mouse mAb, Pharmigen) overnight at 4° C. After extensive washing in PBS, artery sections were incubated with biotin-anti-mouse (1:500; Jackson Immunoresearch) followed by Vectastain® ABC (Vector Labs). Staining was developed using NovaRed™ peroxidase substrate kit (Vector Labs). BrdU index was the percentage of BrdU positive cells of total nuclei in intima, media and advantitia. Sections were counterstained with hematoxylin prior to dehydration and mounting.

Results

Expression of Nogo-B in Femoral Artery After Injury

Figure 10:
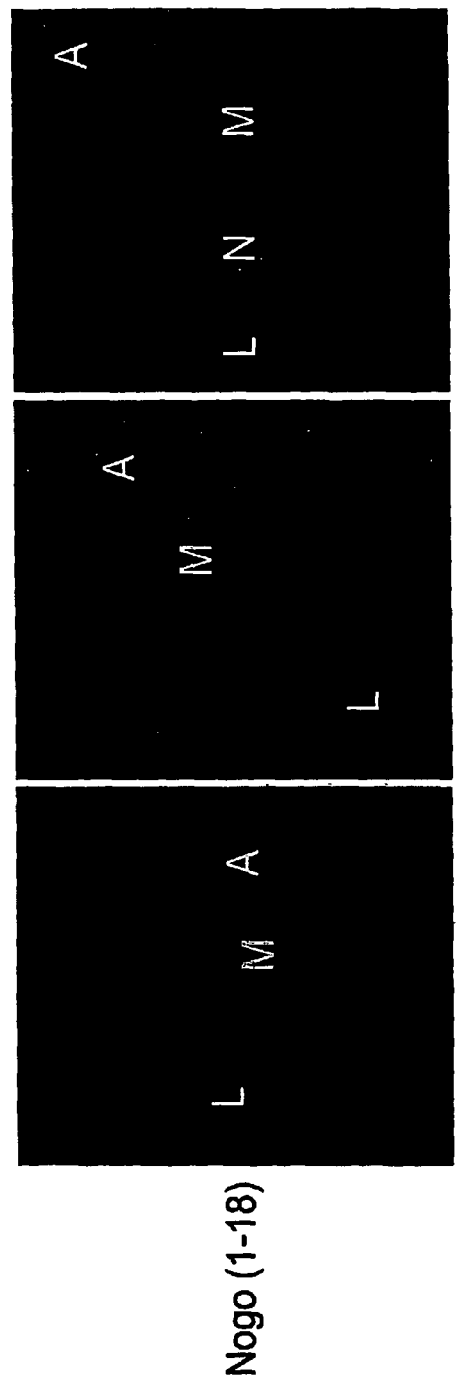
FIG. 10. Nogo expression decreases after injury and by 21 days is almost completely gone from vessel wall. Femoral arteries from normal and injured mice were stained with anti-Nogo (1-18), which stains Nogo-B red (in FIG. 10, the red stain shows up as gray on a black background). As FIG. 10 shows, at 10 days post-injury, there is typically little neointima, but the smooth muscle of the medial layer change phenotype and begin to proliferate and migrate, the expression of Nogo-A/B within the media dramatically decreases. Within 21 days when there is extensive neointima present, there is negligible expression of Nogo-A/B within the vessel. These data suggest that Nogo disappears from the vessel wall as a consequence of vessel injury and its loss correlates with neointima formation. L: lumen. M: media. A: adventitia. N: neointima.

Femoral arteries from normal and injured mice were stained with anti-Nogo (1-18), which stains Nogo-B red. As FIG. 10 shows, at 10 days post-injury there is typically little neointima, but the smooth muscle of the medial layer change phenotype and begin to proliferate and migrate, the expression of Nogo-A/B within the media dramatically decreases. Within 21 days when there is extensive neointima present, there is negligible expression of Nogo-A/B within the vessel. These data suggest that Nogo disappears from the vessel wall as a consequence of vessel injury and its loss correlates with neointima formation. See FIG. 10.

Loss of Nogo-B Enhances Neointima Formation

Figure 11:
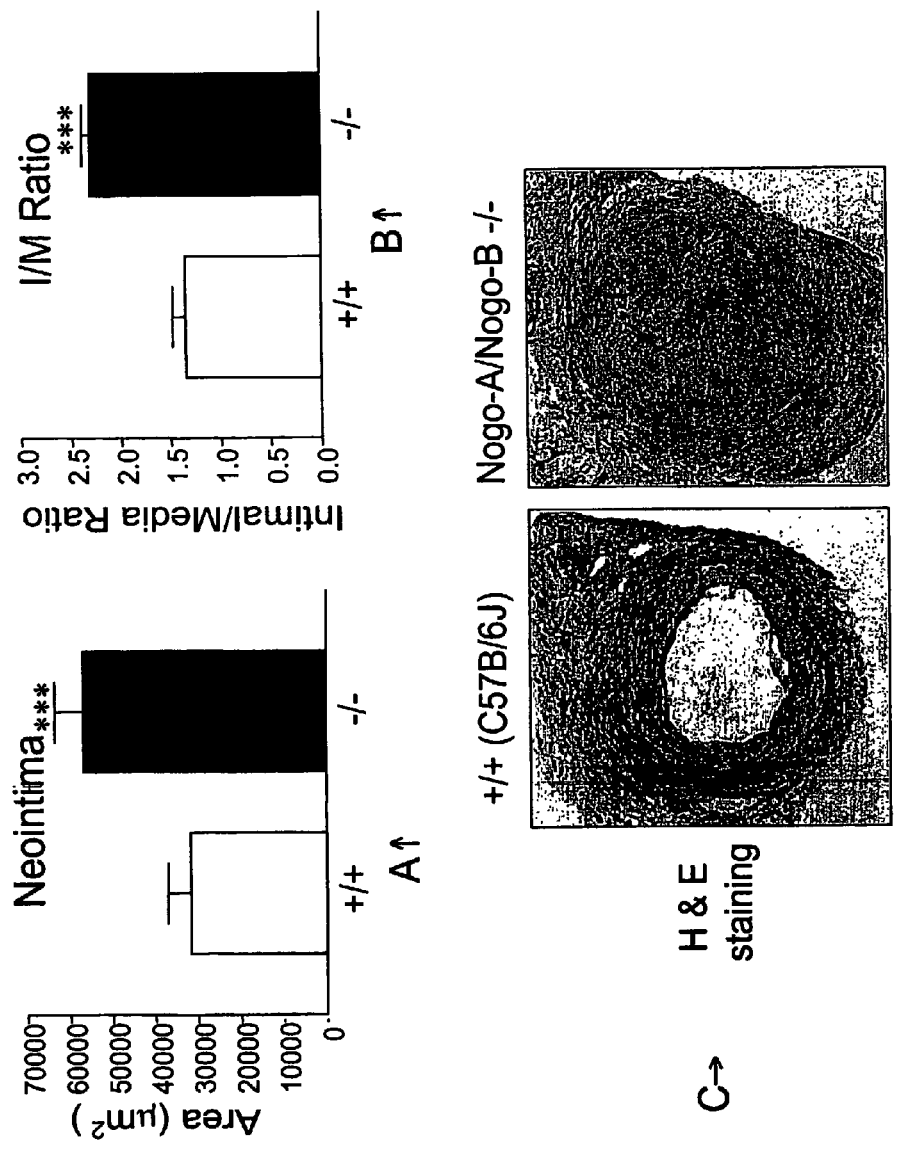
FIG. 11. Loss of Nogo-B promotes pathological inward remodeling FIG. 11A & B: Intimal area (FIG. 11A) and intima/media (I/M) ratio (Figure 11B) were quantified morphometrically three weeks after injury.
Figure 12:
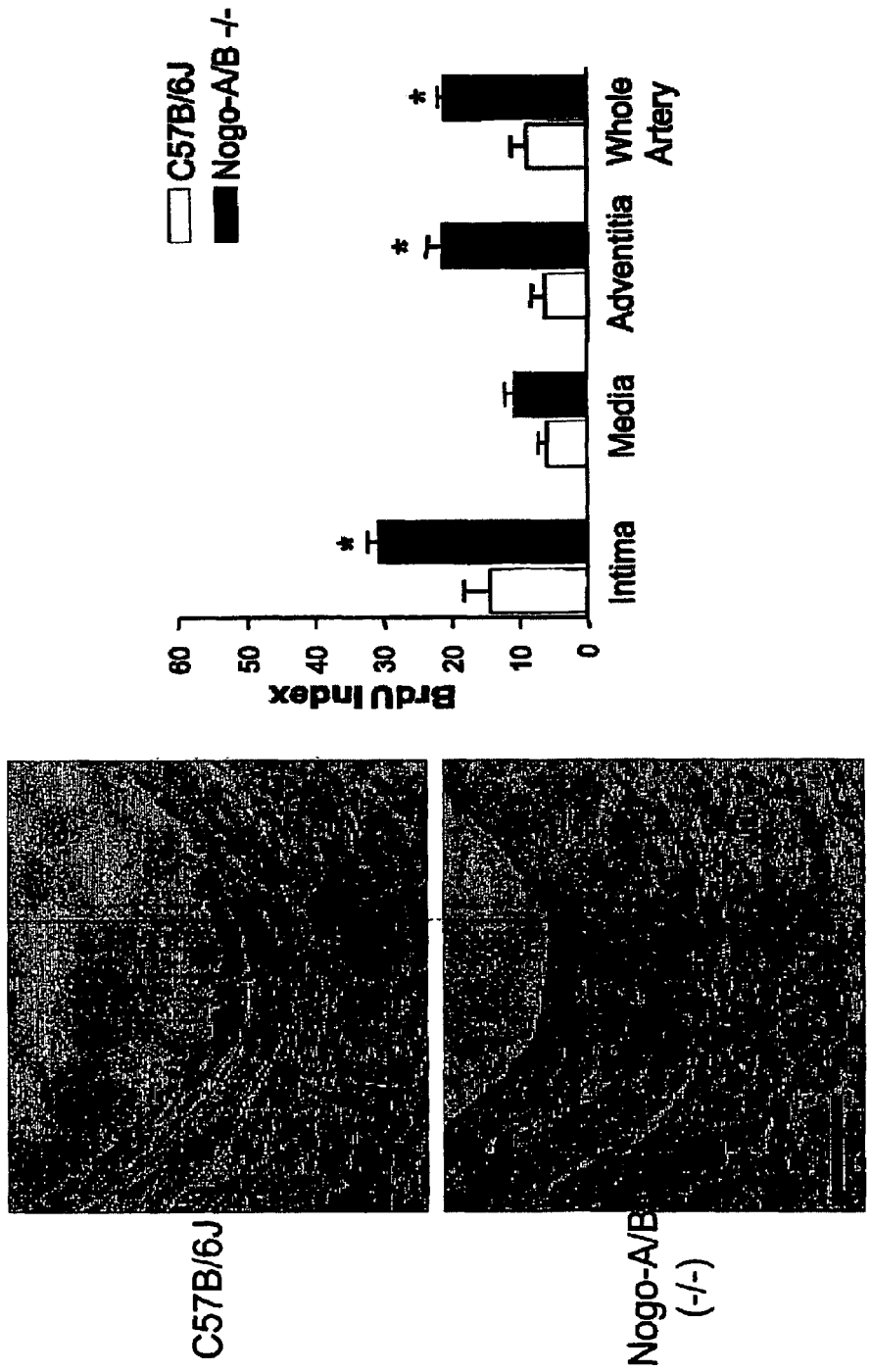
FIG. 12. Nogo-A/B (−/−) mice show enhanced cellular proliferation two weeks after injury.

Since the expression of Nogo-B appears to be associated with neointimal progression, we examined whether the genetic loss of Nogo-A/B would lead to enhanced intimal expansion. As above, femoral arterial injury was performed in WT mice and Nogo A/B (−/−) littermate mice that were age and sex matched. Three weeks after injury, Nogo A/B (−/−) mice exhibited strikingly enhanced neointima formation compared to control mice, and in some cases, complete occlusion of the femoral artery was seen. FIG. 11 shows representative hematoxylin and eosin (H & E) stained femoral arteries of WT and Nogo-A/B (−/−) mice three weeks after injury. All Nogo-A/B (−/−) mice demonstrated a blackening of the toes after injury, consistent with a flow-limiting stenosis (data not shown). Quantitative morphometry of injured vessels reveals a marked reduction in lumen area and increased intimal area as well as intima to media (I/M) ratio in Nogo-A/B (−/−) mice when compared to WT control (Nogo-B (+)) mice. There was no significant difference in medial area, or overall vessel size, as quantified by internal elastic lamina (IEL) and external elastic lamina (EEL) diameters, in Nogo A/B (−/−) mice. See FIG. 12B.

BrdU Labeling and Staining of Mice Arteries

BrdU immunostaining was performed in vessels from control (C57BL/6J; Nogo-B (+)) mice and Nogo-A/Nogo-B (−/−) mice, two weeks after injury to assess proliferation during the remodeling response two weeks post-injury. The increased cellularity found in injured vessels from the Nogo A/B (−/−) mice is associated with a marked increase in cellular proliferation in primarily the intimal and adventitial layers of the vessel wall.

Together, these results are consistent with markedly enhanced pathological neointimal formation and luminal remodeling which is dependent on a loss of Nogo-A/B. See FIG. 12.

Example 9

Overexpression of Nogo-B in Wild-Type Vessels Decreases Intima Formation After Vessel Injury To assess the role of Nogo-B in vessel remodeling wire injury of the femoral artery was used as a model of luminal remodeling and neointima formation. In this example, a guide wire is used to denude the endothelium and cause trauma to the media.

Methods and Materials

Cell Culture

HEK293T cells were cultured in high glucose DMEM with 10% (v/v) FCS. All media were supplemented with 2 mM L-glutamine, 100 units/ml penicillin, and 100 mg/ml streptomycin.

Mice Models

Wild type (WT) C57BL/6J mice were used determine the effect of overexpression of Nogo-B after vessel injury. Ad β-Gal or Ad Nogo-B ($3 \times 10^8$ PFU) was delivered by painting the adventitia side of the femoral artery with 50 µl of adenovirus (15 µl)/30% Pluronic-127 gel (35 µl, Sigma) mixture immediately after injury. Injured femoral arteries were collected 1 week after surgery.

Production of Adenovirus

Replication-deficient adenovirus expressing HA tagged Nogo-B (Ad Nogo-B) was generated using the AdEasy system by subcloning HA-tagged Nogo-B into pShuttleCMV vector. For homologous recombination, pShuttleCMV-Nogo-B-HA was electroporated into BJ5183 competent cells containing AdEasy vector. The viruses were amplified in HEK293 cells, purified using CsCl, and titered by cytopathic effect (CPE).

Femoral Artery Injury and Adenoviral Transduction 8-10 week old C57BL/6J mice were anesthetized with ketamine/xylazine (79.5 mg/kg ketamine, 9.1 mg/kg xylazine) and femoral arterial injury, adenoviral infection and morphometry were performed. Ad β-Gal or Ad Nogo-B ($3 \times 10^8$ PFU) was delivered by painting the adventitia side of the femoral artery with 50 µl of adenovirus (15 µl)/30% Pluronic-127 gel (35 µl, Sigma) mixture immediately after injury. Injured femoral arteries were collected 1 week after surgery.

Histology

After sacrifice, tissue was perfusion fixed with 4% paraformaldehyde in PBS, PH 7.4 at 100 mm Hg pressure or fresh femoral arteries were taken and embedded in O.C.T (Tissue-Tek Elkhart, Ind.). Cryosections (5 µm) of arteries were obtained for hematoxylin/eosin (H & E) and elastic staining (EVG).

Results

Figure 13:
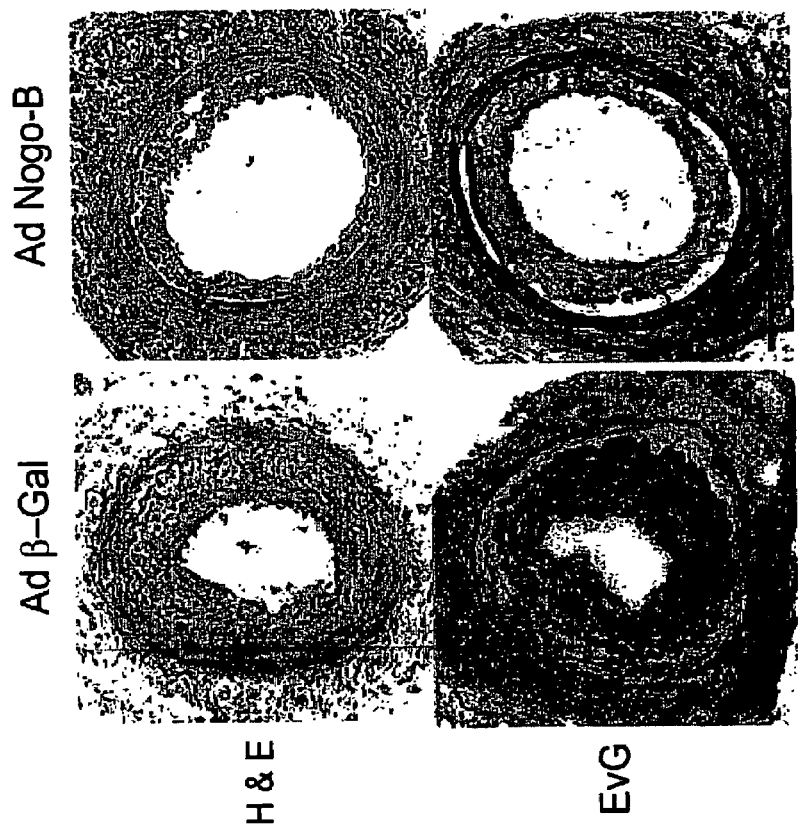
FIG. 13. Ad-Nogo-B decreases neointimal expansion in wild-type mice. Murine blood vessels were injured and immediately thereafter transduced with either Ad-β-gal (which does not rescue Nogo-B deficiency) or Ad-Nogo-B (which does rescue Nogo-B deficiency). Three weeks after injury, neointima is thickened (greater neointima proliferation) in vessels transduced with Ad-β-gal, compared with vessels transduced with Ad-Nogo-B.

Overexpression of Nogo-B in Nogo-A/B (−/−) Mice Prevents Injury-Induced Neointimal Expansion Murine blood vessels were injured and immediately thereafter transduced with either Ad-β-gal (which does not rescue Nogo-B deficiency) or Ad-Nogo-B (which does rescue Nogo-B deficiency). Three weeks after injury, neointima is thickened (greater neointima proliferation) in vessels transduced with Ad-β-gal, compared with vessels transduced with Ad-Nogo-B. See FIG. 13.

Figure 14:
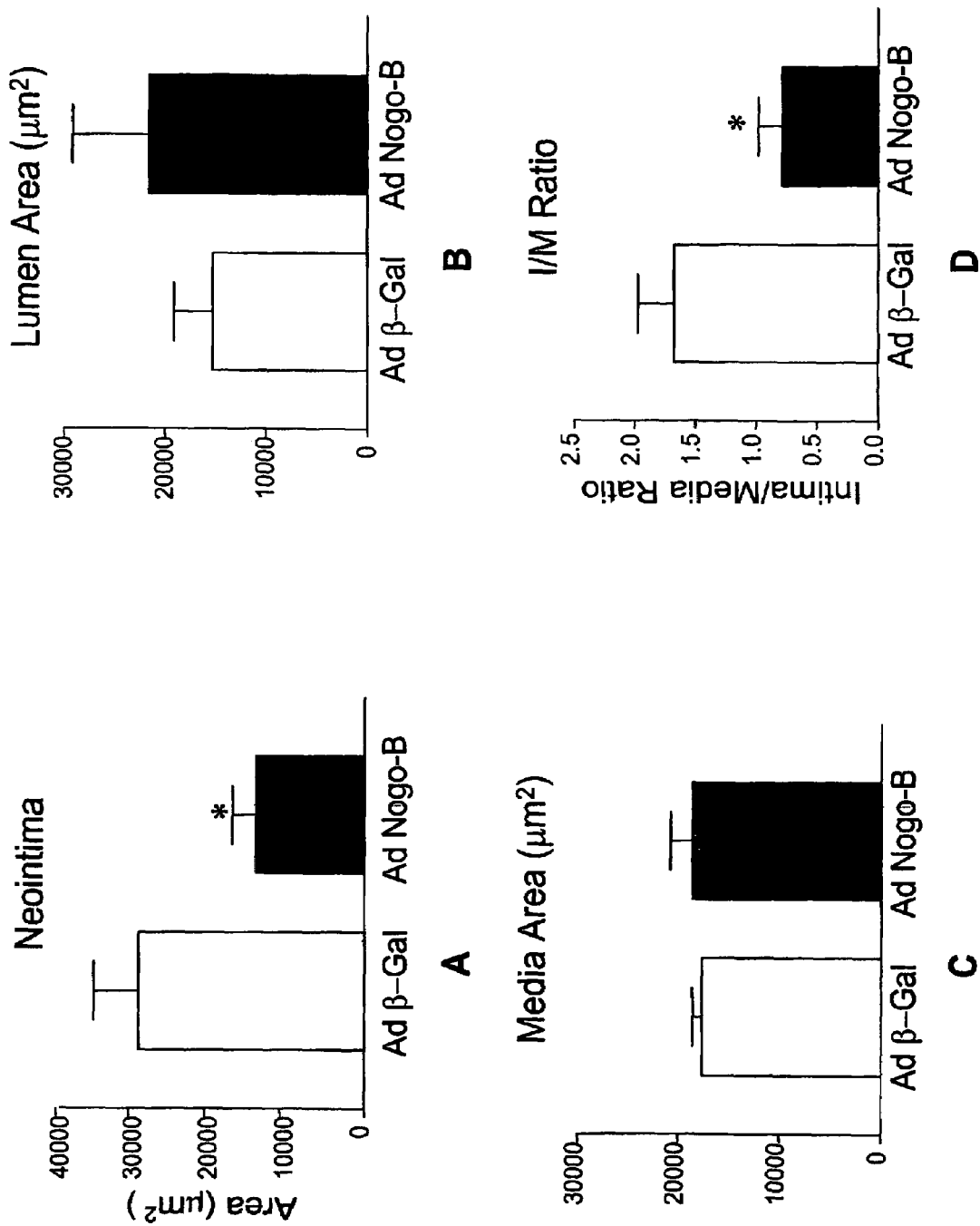
FIG. 14. Murine blood vessels were injured and immediately thereafter transduced with either Ad-β-gal (which does not rescue Nogo-B deficiency) or Ad-Nogo-B (which does rescue Nogo-B deficiency). Intimal area (FIG. 14A), lumen area (FIG. 14B), media area (14C) and intima/media (I/M) ratio (FIG. 14D) were quantified morphometrically three weeks after injury. Vessels transduced with Ad-β-gal showed an increase in intimal expansion (intimal area and I/M ratio. Conversely, vessels transduced with Ad-Nogo-B showed a decrease in intimal expansion (intimal area) and I/M ratio. Lumen area and medial area are greater in Ad-Nogo-B-transduced vessels relative to lumen area and medial area in Ad-β-gal-transduced vessels.

Intimal area (FIG. 14A), lumen area (FIG. 14B), media area (14C)and intima/media (I/M) ratio (FIG. 14D) were quantified morphometrically three weeks after injury. Vessels transduced with Ad-β-gal showed an increase in intimal expansion (intimal area and I/M ratio). Conversely, vessels transduced with Ad-Nogo-B showed a decrease in intimal expansion (intimal area) and I/M ratio. Lumen area and medial area are greater in Ad-Nogo-B-transduced vessels relative to lumen area and medial area in Ad-β-gal-transduced vessels. These data suggest that transduction of wild-type vessels with Ad Nogo-B decreases neointimal proliferation after injury. See FIG. 14.

Example 10

Reconstitution of Nogo-B in Nogo-A/B (−/−) Vessels

To assess the role of Nogo-B in vessel remodeling wire injury of the femoral artery was used as a model of luminal remodeling and neointima formation. In this example, a guide wire is used to denude the endothelium and cause trauma to the media.

Methods and Materials

Cell Culture

HEK293T cells were cultured in high glucose DMEM with 10% (v/v) FCS. All media were supplemented with 2 mM L-glutamine, 100 units/ml penicillin, and 100 mg/ml streptomycin.

Mice Models

Nogo-A/B (−/+) mice were back crossed 7 generations onto a C57BL/6J background and used to generate wild-type (WT) and Nogo-A/B (−/−) littermate mice. Ad β-Gal or Ad Nogo-B ($3 \times 10^8$ PFU) was delivered by painting the adventitia side of the femoral artery with 50 µl of adenovirus (15 µl)/30% Pluronic-127 gel (35 µl, Sigma) mixture immediately after injury. Injured femoral arteries were collected 3 weeks after surgery.

Production of Adenovirus

Replication-deficient adenovirus expressing HA tagged Nogo-B (Ad Nogo-B) was generated using the AdEasy system by subcloning HA-tagged Nogo-B into pShuttleCMV vector. For homologous recombination, pShuttleCMV-Nogo-B-HA was electroporated into BJ5183 competent cells containing AdEasy vector. The viruses were amplified in HEK293 cells, purified using CsCl, and titered by cytopathic effect (CPE).

Femoral Artery Injury and Adenoviral Transduction

Nogo-A/Nogo-B (−/+) mice were back crossed 7 generations onto a C57BL/6J background and used to generate wild-type (WT) and Nogo-A/B (−/−) littermate mice. Male, 8-10 week old Nogo-A/B (−/−) or WT littermate mice were anesthetized with ketamine/xylazine (79.5 mg/kg ketamine, 9.1 mg/kg xylazine) and femoral arterial injury, adenoviral infection and morphometry were performed. Ad β-Gal or Ad Nogo-B ($3 \times 10^8$ PFU) was delivered by painting the adventitia side of the femoral artery with 50 µl of adenovirus (15 µl)/30% Pluronic-127 gel (35 µl, Sigma) mixture immediately after injury. Injured femoral arteries were collected 3 weeks after surgery.

Histology

After sacrifice, tissue was perfusion fixed with 4% paraformaldehyde in PBS, PH 7.4 at 100 mm Hg pressure or fresh femoral arteries were taken and embedded in O.C.T (Tissue-Tek Elkhart, Ind.). Cryosections (5 µm) of arteries were obtained for hematoxylin/eosin and elastic staining.

Results

Reconstitution of Nogo-B in Nogo-A/B (−/−) Mice Prevents Injury-Induced Neointimal Expansion Murine blood vessels were injured and immediately thereafter transduced with either Ad-β-gal (which does not rescue Nogo-B deficiency) or Ad-Nogo-B (which does rescue Nogo-B deficiency). Three weeks after injury, neointima is thickened (greater neointima proliferation) in vessels transduced with Ad-β-gal, compared with vessels transduced with Ad-Nogo-B. See FIG. 15C. Intimal area (FIG. 13A) and intima/media (I/M) ratio (FIG. 15B) were quantified morphometrically three weeks after injury. Vessels transduced with Ad-β-gal showed an increase in intimal expansion (intimal area (FIG. 15A) and I/M ratio (FIG. 15B). Conversely, vessels transduced with Ad-Nogo-B showed a decrease in intimal expansion (intimal area (FIG. 15A) and I/M ratio (FIG. 15B). These data suggest that transduction of vessels with Ad Nogo-B rescues the genetic loss of Nogo A/B. See FIG. 15.

Example 11

Determination of the Extent of Hind-Limb Ischemia in Nogo-A/B Knockout Mice

To assess the role of Nogo-B in remodeling in ischemia driven arteriogenesis and angiogenesis, a hindlimb ischemia model was used. In this example, the proximal end of femoral artery, proximal site of popliteal artery and distal portion of saphenous artery were ligated and an arteriectomy was performed.

Methods and Materials

Mice Models

Nogo-A/Nogo-B-deficient were used as described in Example 6, above. C57BL/6J mice were used as a wild-type model (Nogo-A/Nogo-B (+/+), as in Example 6, above.

Model of Hindlimb Ischemia

All surgical procedures were done under ketamine/xylazine (79.5 mg/kg ketamine, 9.1 mg/kg xylazine) anesthesia. After anesthesia, left common femoral artery was gently exposed from the inguinal ligament to proximal part of the popliteal artery and the saphenous artery by blunted dissection. The accompanying femoral nerve and femoral vein were dissected free from the artery. The proximal end of femoral artery, proximal site of popliteal artery and distal portion of saphenous artery were ligated by 9-0 nylon suture (USSC, Norwalk, Conn.). All branches between inguinal ligament and popliteal artery were cauterized, and arteriectomy was performed. The incision was closed by 6-0 nylon suture. Blood flow of left (ischemic) and right (non-ischemic) limbs were measured on gastronomic muscle pre-surgery, 30 minutes post-surgery, 2 weeks and 4 weeks after surgery by using PeriFlux system with Laser Doppler Perfusion Module (LDPU) unit (Perimed, Inc. North Royalton, Ohio). Deep measurement probe was used to ensure a deep muscle flow measurement. Clinical score for spontaneous mobility (YCS) of each mouse was also taken pre-surgery, post-surgery, 3 days, 2 weeks and 4 weeks after surgery. Clinical score (YCS): Normal=0; Pale of foot or gait abnormalities=1; Gangrenous tissue<half foot w/o lower limb muscle necrosis=2; Gangrenous tissue<half foot w/lower limb muscle necrosis=3; Gangrenous tissue>half foot=4; Loss half of lower limb or more=5

Results

Loss of Nogo-B Impairs Flow Recovery After Surgery

Figure 16:
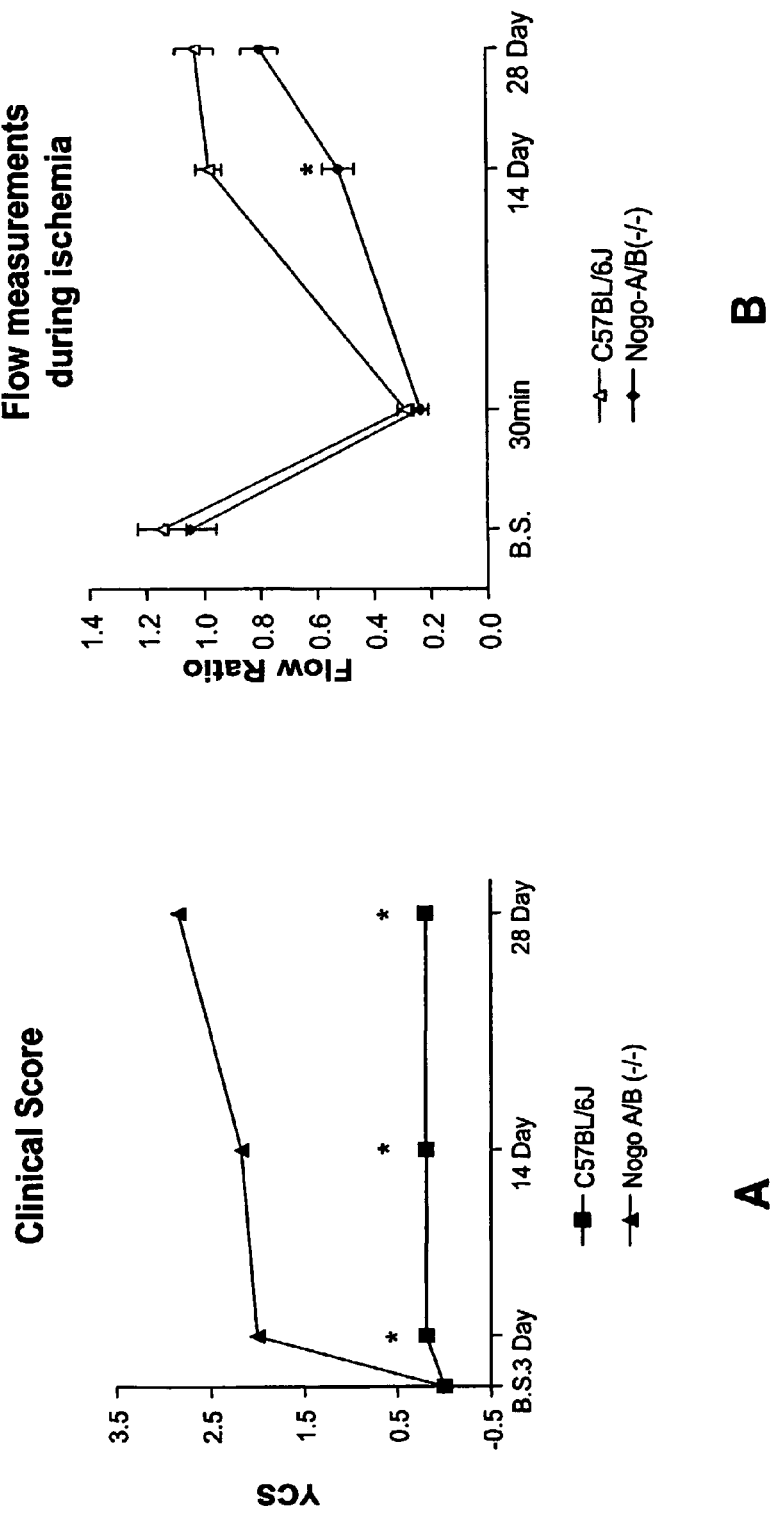
FIG. 16. Hindlimb ischemia in Nogo-A/B (−/−) knockout mice.

The measurement of lower limb blood flow was performed using a Deep Laser Doppler prior to surgery as well as 30 minutes, 14 and 28 days after surgery to induce ischemia. Measurements were taken from both the ischemic and non-ischemic limb to calculate the ratio of flow (a ratio of 1 depicts equal flow to both limbs). In contrast to normal mice (C57B16J), there was decreased recovery of lower limb blood flow at 14 and 28 days post-surgery in Nogo-A/B (−/−) mice. See FIG. 16B.

Loss of Nogo-B Impairs Spontaneous Mobility

Gross examination of the limbs using the YCS clinical score for spontaneous mobility at 3, 14 and 28 days further demonstrated impaired recovery of blood flow to the lower limb of Nogo-A/B (−/−) mice. Gangrenous tissue and in some cases lower limb muscle necrosis was observed in these mice. See FIG. 16A.

Together, these results are consistent with markedly impaired angiogenesis and arteriogenesis which are dependent on a loss of Nogo-A/B. See FIG. 16.

The above preferred embodiments and examples are given to illustrate the scope and spirit of the present invention. The embodiments and examples described herein will make apparent to those skilled in the art other embodiments and examples. These other embodiments and examples are within the contemplation of the present invention.

What is claimed is:

1. A method for promoting endothelial cell adhesion, spreading and migration in treating a condition or disease characterized by pathological vascular remodeling in a subject in need thereof, said method comprising administering a composition comprising Nogo-B or a fragment of Nogo-B comprising 1- 200 of the N-terminus of Nogo-B that retains a biological activity of Nogo-B, wherein said biological activity is selected from the group consisting of promoting endothelial cell adhesion, spreading and migration and wherein the pathological vascular remodeling is in response to blood vessel injury.

2. The method according to claim 1, wherein the disease or condition is selected from the group consisting of: hypertension, restinosis, transplant vasculopathy, arteriosclerosis, ischemia, pulmonary hypertension, asthma, myocardial infarction and cerebrovascular infarction.

3. The method according to claim 1, wherein the disease or condition is ischemia.

* * * * *